(12) United States Patent
Almiñana Domènech et al.

(10) Patent No.: US 10,512,603 B2
(45) Date of Patent: Dec. 24, 2019

(54) **FERMENT EXTRACT OF *EUPENICILLIUM CRUSTACEUM* AND COSMETIC USE THEREOF**

(71) Applicant: LUBRIZOL ADVANCED MATERIALS, INC., Cleveland, OH (US)

(72) Inventors: Núria Almiñana Domènech, Barcelona (ES); Albert Soley Astals, Barcelona (ES); Nuria García Sanz, Alicante (ES); Gemma Mola Llobera, Barcelona (ES); José Darias, La Laguna (ES); Mercedes Cueto, La Laguna (ES)

(73) Assignee: LUBRIZOL ADVANCED MATERIALS, INC., Cleveland, OH (US)

( * ) Notice: Subject to any disclaimer, the term of this patent is extended or adjusted under 35 U.S.C. 154(b) by 0 days.

(21) Appl. No.: 15/555,166

(22) PCT Filed: Mar. 2, 2016

(86) PCT No.: PCT/IB2016/051181
§ 371 (c)(1),
(2) Date: Sep. 1, 2017

(87) PCT Pub. No.: WO2016/139602
PCT Pub. Date: Sep. 9, 2016

(65) Prior Publication Data
US 2018/0042840 A1    Feb. 15, 2018

(30) Foreign Application Priority Data
Mar. 5, 2015    (EP) .................................... 15382099

(51) Int. Cl.
*A61K 8/9728*    (2017.01)
*A61Q 19/02*    (2006.01)
*A61Q 19/08*    (2006.01)
*A61K 8/99*    (2017.01)
*C12R 1/645*    (2006.01)
*C12N 1/14*    (2006.01)
*A61Q 19/00*    (2006.01)

(52) U.S. Cl.
CPC .............. *A61K 8/9728* (2017.08); *A61K 8/99* (2013.01); *A61Q 19/00* (2013.01); *A61Q 19/02* (2013.01); *A61Q 19/08* (2013.01); *C12N 1/14* (2013.01); *C12R 1/645* (2013.01); *A61K 2800/85* (2013.01)

(58) Field of Classification Search
CPC ... A61K 8/9728; A61K 2800/85; A61Q 19/02
See application file for complete search history.

(56) References Cited

U.S. PATENT DOCUMENTS

| 2005/0019282 A1 | 1/2005 | Rendon |
| 2007/0128136 A1 | 6/2007 | Yoo et al. |
| 2007/0274937 A1 | 11/2007 | Dal Farra et al. |

FOREIGN PATENT DOCUMENTS

| JP | 61-143314 A | 7/1986 |
| JP | 02-268679 A | 11/1990 |
| KR | 2012-0140527 A | 12/2012 |
| WO | WO 2005/107697 A1 | 6/2007 |

OTHER PUBLICATIONS

Li, (Anti-aging cosmetics and its efficacy assessment methods), 2015.*
Bonta et al., "The process of ageing reflected by histological changes in the skin," Rom J Morphol. Embryol. vol. 54, pp. 797-804 (2013).
Costin, "Human skin pigmentation: melanocytes modulate skin color in response to stress," FASEB Journal, vol. 21(4), pp. 976-94 (2007).
Fujimoto, et al., "Immunomodulatory constituents from an Ascomycete, Eupenicillium crustaceum, and revised absolute structure of Macrophorin D.," Journal of Natural Products, vol. 64, No. 9, pp. 1234-1237 (2001).
Hearing. "The melanosome: the perfect model for cellular response to the environment," Pigment Cell Res. 13 Suppl. 8, pp. 23-24 (2000).
Hipler, et al., "Biofunctional Textiles and the Skin," Curr. Probl. Dermatol. vol. 33, pp. 35-41 (2006).
Hoashi "MART-1 is required for the function of the melanosomal matrix protein PMEL17/GP100 and the maturation of melanosomes," J Biol. Chem. vol. 280, No. 14, pp. 14006-14016 (2005).
Ito, et al., "Chemical analysis of melanins and its application to the study of the regulation of melanogenesis," Pigment Cell Res. 13 Suppl. 8, pp. 103-109 (2000).
Kim, et al., "Melanocins A, B and C, new melanin synthesis inhibitors produced by Eupenicillium shearii. I. Taxonomy, fermentation, isolation and biological properties," Journal of Antibiotics (Tokyo), vol. 56, No. 12, pp. 993-999 (2003).
Leal, et al., "Chemical and structural similarities in wall polysaccharides of some *Penicillium, Eupenicillium*, and *Aspergillus* species," FEMS Microbiology Letters, vol. 90, No. 2, pp. 165-168 (1992).
Malcolm et al., "Controlled release of a model antibacterial drug from a novel self-lubricating silicone biomaterial," J. Cont. Release, 97(2) pp. 313-320 (2004).
Mycobank, et al., "Eupenicillium crustaceum," pp. 1-11 (2016), downloaded at http://www.mycobank.org/Biolomics.aspx?Table=Mycobank&MycoBankNr_=101937 on Aug. 31, 2017.
Nelson, "Application of microencapsulation in textiles," Int. J. Pharm., 242(1-2), pp. 55-62 (2002).

(Continued)

*Primary Examiner* — Zohreh A Fay
(74) *Attorney, Agent, or Firm* — Thoburn Dunlap; Ann Skerry

(57) ABSTRACT

A ferment extract from a bacterial strain the *Eupenicillium crustaceum* species useful in the cosmetic treatment and/or care of the skin, mucous membranes, hair and/or nails and cosmetic uses of same.

20 Claims, No Drawings

(56) References Cited

OTHER PUBLICATIONS

Pageon, "Reaction of glycation and human skin: the effects on the skin and its components, reconstructed skin as a model," Pathol. Biol. (Paris), vol. 58(3), pp. 226-231 (2010).
Ranu, et al., "Periorbital hyperpigmentation in Asians: an epidemiologic study and a proposed classification," Dermatol. Surg. vol. 37(9), pp. 1297-303 (2011).
Schaab, et al., "Impregnating Fabrics with Microcapsules," HAPPI pp. 84-86 (May 1986).
Stillman, "Jaundice. Clinical Methods: The History, Physical, and Laboratory Examinations," 3rd edition, Chapter 87 (1990).
CTFA International Cosmetic Ingredient Dictionary and Handbook, $12^{th}$ Edition (2008).
Wilkinson, et al., "Harry's Cosmeticology," Seventh Edition Longman House, Essex, G.B. pp. 50-73 and 757-799 (1982).
Yamada "Accelerated differentiation of melanocyte stem cells contributes to the formation of hyperpigmented maculae," Exp. Dermatol., vol. 23(9), pp. 652-658 (2014).
Yamaguchi "Regulation of skin pigmentation and thickness by Dickkopf 1 (DKK1)," J Investig. Dermatol. Symp. Proc., vol. 14(1), pp. 73-75 (2009).
Zhang, et al., "Silencing of GPNMB by siRNA inhibits the formation of melanosomes in melanocytes in a MITF-independent fashion," 2012 vol. 7(8), pp. 1-10 (2012).

\* cited by examiner

FERMENT EXTRACT OF *EUPENICILLIUM CRUSTACEUM* AND COSMETIC USE THEREOF

This application claims the benefit of PCT/IB2016/051181, filed Mar. 2, 2016, and EP15382099.8, filed Mar. 5, 2015, from which the PCT application claims priority, the disclosures of all of which are incorporated herein by reference in their entireties.

FIELD OF THE INVENTION

The disclosed technology relates to a ferment extract from a strain of *Eupenicillium crustaceum* species which is useful in the cosmetic treatment and/or care of skin, mucous membranes, hair and/or nails. In particular, the ferment extract is active in the alleviation or prevention of the symptoms of the aging of skin, and in the lightening of color or depigmentation or whitening of skin.

BACKGROUND OF THE INVENTION

Aging of the skin is a complex process induced by chronological and environmental factors (mainly UV radiation). Signs or symptoms of skin aging include the loss of skin elasticity and firmness, the appearance of features such as wrinkles and furrows, dark under-eye circles, puffy eyes, eye bags, solar lentigines (age spots) and mottled skin. The first signs of skin aging are usually evident on a person's face, specifically in the region around the eyes. These include the presence of dark eye circles (periorbital hyperpigmentation), puffy eyes (periorbital puffiness), eye bags (infraorbital palpebral bags), and wrinkles (for example, periorbital wrinkles). The presence of the signs of aging on a person's skin, especially their face, is aesthetically undesirable. Younger looking skin, that is, skin with reduced symptoms of aging, is desired.

The skin, mucous membranes, hair and/or the nails provide a physical barrier between an organism and its environment. The skin is composed of two principal layers, the epidermis and the dermis. The dermis is the thickest layer (having an approximate thickness of 90% of the thickness of the skin) and contains collagen, elastin, several differentiated structures such as blood vessels and many cell types such as fibroblasts (which synthesize collagen and elastin). The epidermis is composed of keratinocytes, melanocytes and Langerhans cells, with the main cell population composed of keratinocytes.

Collagen is the most abundant protein in the skin's connective tissue and plays an important structural role in the skin. It forms a mesh like structure in the skin connective tissue that helps support new cells as they grow while providing the needed flexibility. There is continual collagen synthesis and degradation in the skin, and the balance between them determines both the tensile strength and elasticity of the skin. Elastin is a protein in the connective tissue that is elastic. Elastin is helps to keep the skin flexible but tight, providing a bounce-back reaction if the skin is pulled. The aging process is accompanied by degeneration and lysis of both collagen fibers and elastic fibers in the skin. The gradual disappearance of elastic fibers in the skin results in the progressive loss of skin elasticity. The degeneration and lysis of collagen fibers results in the skin losing resistance (firmness). A further consequence of connective fibers lysis in the dermis is the gradual reduction of the dermis thickness as a whole, particularly through the reduction in collagen fibers. [Bonta M, Daina L, Muţiu G. *The process of ageing reflected by histological changes in the skin. Rom J Morphol. Embryol.* 2013; 54 (3 Suppl.):797-804]

Another factor in the aging of the skin is the appearance of Advanced Glycosylation End Products (AGEs). AGEs are obtained from a reaction called glycation involving sugar and protein. The presence of these products in the skin changes the physical, biomechanical (the skin stiffens and loses elasticity) and biological properties (modulation of the synthesis, degradation of the matrix by cells). AGEs can modulate the expression of proteins of the extracellular matrix (ECM) as collagen, and they can also modify the expression and synthesis of the enzymes which are responsible for its degradation (elastase and metalloproteinases enzymes) [Pageon, H. *Reaction of glycation and human skin: the effects on the skin and its components, reconstructed skin as a model. Pathol. Biol.* (*Paris*). 2010 June; 58(3):226-31]. The result is reduced elasticity and thickness of the skin. In skin, glycation of collagen Type I has been linked to the development of skin dullness and the decrease of skin elasticity.

As a result of reduced elasticity, firmness and thickness, wrinkles in the skin can appear, such as those that appear around the eye. There is a need to provide an active agent which can help prevent collagen degradation and/or stimulate collagen production in the skin. There is a need to provide an active agent which can help prevent elastin degradation and/or stimulate elastin production in the skin. There is a need to provide an active agent that can inhibit the formation of AGEs in the skin. Such active agents can be useful in the treatment skin to prevent or alleviate signs of aging.

The aging process also affects the vasculature in the skin. Vascular changes include the thinning of capillary walls and the slowing of microcirculation. Alteration of the blood vessel walls causes changes in vascular permeability and can result in the appearance of interfibrillar edema [Bonta M, Daina L, Muţiu G. *The process of ageing reflected by histological changes in the skin. Rom J Morphol. Embryol.* 2013; 54(3 Suppl.):797-804]. Thus one of the signs of aging is the accumulation of interstitial fluid around and under the eyes, for example, puffy eyes and eye bags (also known as bags under the eye). These are aesthetically unsightly and it is desired that the puffiness of the skin/volume of the bags is reduced. There is a need for active agents that are able to decrease vascular permeability implicated in the edema formed in puffy eyes and eye bags.

As skin ages, it becomes thinner. For example, Bonta et al. note that decreased vascular efficiency, especially in the superficial dermis, produces a series of major effects in the epidermis, by adapting it to the efficiency of vasculature, namely by reducing the number of cell layers, i.e. by reducing the thickness [Bonta M, Daina L, Muţiu G. *The process of ageing reflected by histological changes in the skin. Rom J Morphol. Embryol.* 2013; 54(3 Suppl.):797-804]. This thinness can result in the underlying blood vessels and chromophores (such as bilirubin and melanin) becoming more visible. This is one cause of dark under-eye circles, a very common cosmetic problem affecting the majority of people [Ranu H, Thng S, Goh B K, Burger A, Goh C L. *Periorbital hyperpigmentation in Asians: an epidemiologic study and a proposed classification. Dermatol. Surg.* 2011 September; 37(9):1297-303]. It is believed that this problem is further exacerbated, by the blood vessels becoming leaky with aging and, as a result, bilirubin, a breakdown product of blood, accumulating around the eyes. Specifically, bilirubin is a breakdown product of heme metabolism. Heme is an iron-containing porphyrin found in hemoglobin, myoglobin, and several enzymes of which the hepatic cytochromes are the most important representatives. Approximately 80% of daily bilirubin production derives from senescent red blood cells. These are broken down and iron is removed from the heme molecule and the remaining porphyrin ring is oxidized and cleaved at a single site to form the tetrapyrrole chain structure of biliverdin. Further reduction of the biliverdin results in the formation of bilirubin responsible for the coloration appearing in the infraorbital eyelids as dark under-eye circle [Stillman A E. *Jaundice. Clinical Methods: The History, Physical, and Laboratory Examinations.* 3rd edition. Boston: Butterworths; 1990. Chapter 87]. Dark eye circle is a complex facial cosmetic problem, with multiple causes and these include melanin deposition, venous stasis with hemosiderin deposition, and orbital structural problems. Melanin deposits in the dermis may be congenital or secondary to environmental factors such as excessive exposure to the sun, endogenous or use of exogenous estrogens, pregnancy and breastfeeding. There is a need to provide an active agent that can degrade bilirubin and/or reduce the amount of melanin in the skin, two of the pigments responsible of the pigmentation in dark circles around the eyes.

The signs of aging such as wrinkles, dark under-eye circles, puffy eyes, eye bags can be exacerbated by fatigue, stress, drug and alcohol use, among other factors.

The modification of skin color, including the lightening of skin, for example, of dark eye circles as well as the elimination or attenuation of age spots, is a cosmetic effect desired by many people. Often the aim is to achieve an even skin color. Depigmenting cosmetic products are used to reduce hyperchromia and, typically, depigmenting agents act by inhibiting a melanin biosynthesis route.

Melanins are complex pigments that provide the skin, hair and eyes of mammals with color and photoprotection against ionizing radiation. Melanogenesis is physiological process resulting of the synthesis of the melanin pigments, and is characterized, in summary, by the production process and subsequent distribution of melanin by melanocytes. Mammalian melanocytes produce two chemically distinct types of melanin pigments, the black to brown eumelanin and the yellow to reddish brown pheomelanin, by different enzymes in complex organelles called melanosomes. Both eumelanin and pheomelanin are derived from the common precursor dopaquinone that is formed by tyrosinase (TYR). Tyrosinase is also called polyphenol oxidase and is a copper-containing multifunctional enzyme. It is the key enzyme in the first stage of melanogenesis cascade, catalyzing the conversion of L-tyrosine in L-dopaquinone (Ito S., Wakamatsu K., and Ozeki, H. *Chemical analysis of melanins and its application to the study of the regulation of melanogenesis. Pigment Cell Res.* 2000: 13 Suppl. 8. 103-9). In addition to tyrosinase, two related proteins, termed tyrosinase-related proteins (TRPs), have been shown to regulate eumelanin formation. TRP-1 (Tyrosinase-related protein-1) or DHICA (5,6-dihydroxyindol-2-carboxylic acid oxidase), and TRP-2 (Tyrosinase-related protein-2), also known as dopachrome tautomerase (Hearing. V. J. *The melanosome: the perfect model for cellular response to the environment Pigment Cell Res.* 2000; 13 Suppl. 8, 23-4). Melanin formation also originates in tyrosine oxidation, by the enzyme tyrosinase, to dihydroxyphenylalanine (DOPA) inside melanocytes.

Melanosomes are lysosome-related organelles which have the unique capacity to produce melanin pigment and which progress through four sequential morphological steps as they mature (stage I, II, III and IV). Stage I melanosomes are round, membrane-bound and electron-lucent vesicles that are generally found in the perinuclear area. The transition to Stage II melanosomes involves an elongation of the vesicle, and the appearance within of distinct fibrillar structures. The production of those internal matrix fibers and the maturation from Stages Ito II melanosomes depend on the presence of a structural protein termed Pmel17, (also known as gp100 or SILV). Shortly after its delivery to Stage I melanosomes, Pmel17 is cleaved into several fragments, which form the fibrillar matrix of the organelle. In pigmented cells, melanin is deposited on these fibers, resulting in a progressively pigmented internal matrix, at which time the organelles are termed Stage III melanosomes. In highly pigmented tissues, melanin synthesis and deposition continues until little or no internal structure is visible, at which time they are termed Stage IV melanosomes. Several proteins have been identified as melanosome-specific proteins (Tyr, Trp1, Trp2, MART-1, Pmel17, GPNMB, etc.). MART-1, melanoma-associated antigen recognized by T cells protein (also known as Melan-A), a melanosome-specific proteins, has no detectable enzymatic activity, is highly enriched in early melanosomes (Stage I and/or II melanosomes), and forms a complex with Pmel17 and affects its expression, stability, trafficking, and the processing which is required for melanosome structure and maturation and thus plays an important role in regulating mammalian pigmentation (Hoashi T, Watabe H, Muller J, Yamaguchi Y, Vieira W D, Hearing V J. *MART-1 is required for the function of the melanosomal matrix protein PMEL17/GP100 and the maturation of melanosomes.* J Biol. Chem. 2005 Apr. 8; 280(14):14006-16. Epub 2005 Jan. 28.) GPNMB (glycoprotein (transmembrane) nonmetastatic melanoma protein b), a highly glycosylated type I transmembrane protein, exhibits a high similarity with Pmel17. GPNMB contains several domains related with its functions in melanocytes. It has been confirmed that the arginine-glycine-aspartate (RGD) motif of GPNMB can bind to integrins to regulate the adhesion of melanocytes with keratinocytes, indicating that it is involved in the transfer of melanin. As an important structural protein of melanosomes, GPNMB has proven to be present in all stages (I-IV) of melanosomes, and is especially enriched in mature stages. GPNMB deletion in melanocytes sharply attenuated melanosome formation, indicating a critical role in melanosome synthesis (Zhang P, Liu W, Zhu C, Yuan X, Li D, Gu W, Ma H, Xie X, Gao T. Silencing of GPNMB by siRNA inhibits the formation of melanosomes in melanocytes in a MITF-independent fashion. *PLoS One.* 2012; 7(8):e42955.)

After the production, melanin, within the melanosomes, is transferred to the adjacent keratinocytes through dendrites present in the melanocytes, where it shall be transported and degraded. This melanin transference may occur through three different mechanisms: Cytophagocytosis process of the dendritic end of the melanocyte by the keratinocyte; direct migration of melanosomes of the cytoplasm to the keratinocyte and; release of the melanosomes in the extracellular space and its incorporation to the keratinocytes. Thus, skin pigmentation depends on the number, the chemical nature of melanin and content (the tyrosinase activity), and distribution of melanosomes produced, and transferred by each melanocyte to a cluster of keratinocytes surrounding it.

Increased melanin production due to the direct or indirect stimulation is a defensive reaction of skin in order to protect against solar aggression. After UV irradiation, the melanosomes regroup around the nucleus in order to protect the cell's genetic material and thus, in addition to promoting the skin and hair coloring, melanin promotes photo protection, acting as a sun filter, diffracting or reflecting solar radiation. The melanocyte-keratinocyte complex responds quickly to a wide range of environmental stimuli, often in paracrine and/or autocrine manners. Thus, melanocytes respond to UV-R, agouti signaling protein, melanocyte-stimulating hormone (MSH), endothelins, growth factors, cytokines, etc. After UV-R exposure, melanocytes increase their expression of proopiomelanocortin (POMC, the precursor of MSH) and its receptor melanocortin 1 receptor (MC1-R), TYR and TYRP1, protein kinase C (PKC), and other signaling factors. On the other hand, it is known that UV stimulates the production of endothelin-1 (ET-1) and POMC by keratinocytes and that those factors can then act in a paracrine manner to stimulate melanocyte function. In addition to keratinocytes, fibroblasts, and possibly other cells in the skin produce cytokines, growth factors, and inflammatory mediators that can increase melanin production and/or stimulate melanin transfer to keratinocytes by melanocytes. Melanocyte growth factors affect not only the growth and pigmentation of melanocytes but also their shape, dendricity, adhesion to matrix proteins, and mobility.

α-MSH, ACTH, basic fibroblast growth factor (bFGF), nerve growth factor (NGF), endothelins, granulocyte-macrophage colony-stimulating factor (GM-CSF), steel factor, leukemia inhibitory factor (LIF), and hepatocyte growth factor (HGF) are keratinocyte-derived factors that are thought to be involved in the regulation of the proliferation and/or differentiation of melanocytes, some acting through receptor mediated signaling pathways. It has been shown that in human epidermis, α-MSH and ACTH are produced in and released by keratinocytes and are involved in regulating melanogenesis and/or melanocyte dendrite formation. α-MSH and ACTH bind to a melanocyte-specific receptor, MC1-R, which activates adenylate cyclase through G protein, which then elevates cAMP from adenosine triphosphate. Cyclic AMP exerts its effect in part through protein kinase A (PKA), which phosphorylates and activates the cAMP response element binding protein (CREB) that binds to the cAMP response element (CRE) present in the M promoter of the microphthalmia-associated transcription factor (MITF) gene. The increase in MITF-M expression induces the up-regulation of TYR, TYRP1, and DCT, which leads to melanin synthesis.

Hyperpigmentation is a disorder caused by exaggerated melanin production. Factors such as excessive solar exposure, aging, hormone changes, inflammation, allergies, among others, may cause an unbalance in the melanin production and distribution process, resulting in skin stains. Solar lentigines (also known as senile lentigo, sun-, liver-, or age spots) are circumscribed, pigmented macules, which are usually light brown, but vary in degree of color to jet black. Solar lentigines are typically found on UV-exposed areas of the body (the face, dorsum of the hand, extensor forearm, upper back, and decolletage). They can range anywhere in size from 1 mm up to a few centimeters in diameter and, in areas of severely sun-damaged skin, may coalesce into even larger lesions. There is a desire to provide cosmetic actives that can lighten the color of hyperpigmented skin such as solar lentigines (age spots).

The molecular mechanism currently proposed for the appearance of solar lentigines involves the stimulation of two epidermal cascades, consisting of ET-1/ETBR (initiated by the binding of ET-1 to its receptor, ETBR), and SCF/c-kit (initiated by the binding of Stem cell factor to its receptor c-Kit), and the cross-talk between those two after the UV exposure. Exposure to UV radiation induces an increase in the production of ET-1 by keratinocytes, and its secretion therefore stimulates melanocytes to produce melanin. The potential of keratinocytes located in SL lesional epidermis to produce ET-1 is significantly higher than in perilesional normal controls, and there is an accentuated expression of ETBR transcripts as well. The increased production and localization of ET-1 was paralleled by increased amounts of tyrosinase in melanocytes. Separately, SCF (also produced by keratinocytes) binds to the c-KIT receptor on melanocytes. Solar lentigines lesional epidermis expresses increased levels of SCF mRNA transcripts and protein compared with nonlesional controls. [Costin G E, Hearing V J. *Human skin pigmentation: melanocytes modulate skin color in response to stress. FASEB J.* 2007 April; 21(4):976-94]

However, other cascades in the skin may also contribute to the hyperpigmentation seen in solar lentigines. The Wnt signaling pathway, which triggers the differentiation of melanocyte stem cells, in solar lentigine lesions, is implicated in the accelerated differentiation of melanocyte stem cells was involved in the formation of SLs. The Wnt signaling pathway is closely related to melanocyte biology. This signaling pathway is also important for melanocyte stem cells to trigger the differentiation into follicular melanocytes and epidermal melanocytes. The protein dickkopf WNT signaling pathway inhibitor 1 (DKK1), an inhibitor of the Wnt signaling pathway, prevented melanogenesis and decreased the density of melanocytes. DKK1 suppresses melanocyte function and growth through the regulation of microphthalmia-associated transcription factor (MITF) and b-catenin. [Yamaguchi Y, Morita A, Maeda A, Hearing V J. *Regulation of skin pigmentation and thickness by Dickkopf 1 (DKK1). J Investig. Dermatol. Symp. Proc.* 2009 August; 14(1):73-5.] [Yamada T, Hasegawa S, Inoue Y, Date Y, Arima M, Yagami A, Iwata Y, Takahashi M, Yamamoto N, Mizutani H, Nakata S, Matsunaga K, Akamatsu H. *Accelerated differentiation of melanocyte stem cells contributes to the formation of hyperpigmented maculae. Exp. Dermatol.* 2014 September; 23(9):652-8.]

Thus an active agent which can inhibit a melanin biosynthesis route or act directly on it can have a lightening or depigmenting effect on the skin, such as an active agent that can inhibit tyrosinase activity, inhibit the production of melanin in melanocytes, or affect the expression of genes involved in the melanogenic process, can act as a depigmenting agent. There is a need for a new active agent effective in having a lightening, whitening or depigmenting effect on the skin The present invention sets out to solve some or all of the above-identified problems and meet some or all of the above-identified needs.

SUMMARY OF THE INVENTION

In a first aspect, the invention relates to a ferment extract from a strain of *Eupenicillium crustaceum* species. It has been found that a ferment extract from a strain of *Eupenicillium crustaceum* species is particularly effective in the cosmetic treatment and/or care of the skin, mucous membranes, hair and/or nails.

In the context of this invention, the cosmetic treatment and/or care includes: the depigmentation of or the whitening or the lightening in color of the skin, mucous membranes, hair and/or nails; the depigmentation of or the whitening or the lightening in color of age spots; the depigmentation of or the whitening or the lightening in color of the skin of dark eye circles; the maintenance or improvement of skin luminosity; the alleviation of the symptoms of skin aging;

treatment of skin wrinkles, such as periorbital wrinkles; treatment of dark under-eye circles; treatment of puffy eye; treatment of eye bags; the smoothing out of or reduction of skin wrinkles; the reduction in volume of a puffy eye or of eye bags; the maintenance or improvement of skin elasticity; the maintenance or improvement of skin resistance, firmness or tensile strength.

Surprisingly, the inventors have found that the ferment extract from a strain of *Eupenicillium crustaceum* species is effective in smoothing out skin wrinkles and reducing the volume of puffy eyes or of eye bags. The inventors have also found that the ferment extract from a strain of the *Eupenicillium crustaceum* species is able to promote the synthesis of collagen and elastin, that form the collagen and elastic fibers respectively, can inhibit the enzymes responsible for the degradation of collagen and elastin, and can inhibit the glycation of collagen. Further, they have found that the ferment extract from a strain of the *Eupenicillium crustaceum* species is able to reduce vascular permeability implicated in the edema formed in puffy eyes and eye bags. In one embodiment, the cosmetic treatment and/or care includes the lightening in color, whitening or depigmentation of the skin, mucous membranes, hair and/or nails. Surprisingly, the inventors have found that the ferment extract of the invention is particularly effective in the lightening in color or the depigmentation of hyperpigmented skin such as age spots, and of dark eye circles. The inventors have found that the ferment extract from a strain of the *Eupenicillium crustaceum* species is able to inhibit tyrosinase activity, inhibit the production of melanin in melanocytes and affect the expression of genes involved in the melanogenic process and thus can act as a skin depigmenting/whitening/lightening of color agent. Further, they have found that this effect is more pronounced in hyperpigmented skin, e.g. age spots. They have found that the ferment extract from a strain of the *Eupenicillium crustaceum* species is able to reduce bilirubin and melanin concentration, two of the pigments responsible for the dark pigmentation in the skin of dark circles around the eyes.

In a second aspect, the invention provides the use of a ferment extract from a strain of *Eupenicillium crustaceum* species for the cosmetic treatment and/or care of the skin, mucous membranes, hair and/or nails.

In a third aspect, the invention provides a cosmetic composition comprising a cosmetically effective amount of a ferment extract from a strain of *Eupenicillium crustaceum* species.

In a fourth aspect, the invention provides for the use said composition in the cosmetic treatment and/or care of skin, mucous membranes, hair and/or nails.

In a fifth aspect, the invention provides cosmetic methods for treating the skin comprising the topical administration of a ferment extract from a strain of *Eupenicillium crustaceum* species or compositions comprising same.

DESCRIPTION OF THE INVENTION

The preferred embodiments as set out below are applicable to all the above-mentioned aspects of the invention.

Definitions

In the context of this invention "skin" is understood to be the layers which comprise it, from the uppermost layer or stratum corneum to the lowermost layer or hypodermis, both inclusive. These layers are composed of different types of cells such as keratinocytes, fibroblasts, melanocytes and/or adipocytes among others. In the context of this invention, the term "skin" includes the scalp. The term "skin" includes human skin.

The term "treatment", as used in the context of this specification when it is not accompanied by the qualifications "cosmetic" or "non-therapeutic", means the administration of a compound according to the invention to alleviate or cure a disease or disorder, or reduce or eliminate one or more symptoms associated with this disease or disorder, or alleviate or eliminate the physiological consequences of the disease or disorder.

Where the term "treatment" or "care" is accompanied by the qualification "cosmetic", it means that the treatment or care is non-therapeutic and has the aim of improving the aesthetic appearance of the skin. This can be by improving properties of the skin such as, but not restricted to, the level of hydration, elasticity, firmness, shine, tone or texture, which properties affect the cosmetic appearance of the skin. The term "care" in the context of this specification refers to the maintenance of properties of the skin. The properties of the skin are subject to improvement and maintenance through cosmetic treatment and/or care of the skin both in healthy subjects as well as those who present diseases and/or disorders of the skin and/or mucous membranes, such as and not restricted to, ulcers and lesions on the skin, psoriasis, dermatitis, acne or rosacea, among others.

The term "prevention", as used in this invention, refers to the ability of the active of the invention to prevent, delay or hinder the appearance or development of a disease or disorder or skin property/feature before its appearance.

In the context of this invention, the term "aging" refers to the changes experienced by the skin with age (chronoaging) or through exposure to the sun (photoaging) or to environmental agents such as tobacco smoke, extreme climatic conditions of cold, heat, or wind, chemical contaminants or pollutants, and includes all the external visible and/or perceptible changes through touch, such as and not restricted to, the development of discontinuities on the skin such as wrinkles, fine lines, furrows, irregularities or roughness, increase in the size of pores, loss of elasticity, loss of firmness, loss of smoothness, loss of the capacity to recover from deformation, sagging of the skin such as sagging cheeks, the appearance of bags under the eyes or the appearance of a double chin, among others, changes to the color of the skin such as marks, reddening, bags under the eyes or the appearance of hyperpigmented areas such as age spots or freckles among others, anomalous differentiation, hyperkeratinization, elastosis, keratosis, hair loss, orange-peel skin, loss of collagen structure and other histological changes of the stratum corneum, of the dermis, epidermis, vascular system (for example the appearance of spider veins or telangiectasias) or of those tissues close to the skin, among others. The term "photoaging" groups together the set of processes due to the prolonged exposure of the skin to ultraviolet radiation which result in the premature aging of the skin, and present the same physical characteristics as aging, such as and not restricted to, flaccidity, sagging, changes to the color or irregularities in the pigmentation, abnormal and/or excessive keratinization. The changes of the skin due to aging (e.g. chronoaging, photoaging and/or environmental aging) are also referred to herein as the symptoms or signs of skin aging.

In a first aspect, the present invention relates to a ferment extract from a strain of *Eupenicillium crustaceum* species which is useful in the cosmetic treatment and/or care of the skin, mucous membranes, hair and/or nails. The inventors have found a new cosmetic ingredient; a ferment extract derived from a strain of *Eupenicillium crustaceum* species. Advantageously, this new cosmetic active is derived from natural resources and is surprisingly effective in the cosmetic treatment and/or care of the skin, mucous membranes, hair and/or nails. In particular, it is effective in the alleviating or preventing the signs of skin aging. Further, it is effective in the lightening in color, whitening or depigmentation of skin, mucous membranes, hair and/or nails.

The ferment extract from a strain of *Eupenicillium crustaceum* species used in the invention is the fermentation product of a strain of *Eupenicillium crustaceum* species. The ferment extract is an extract from a strain of *Eupenicillium crustaceum* species that has been subjected to a fermentation process and can be an extract from the cells of the *Eupenicillium crustaceum* species which have been separated out from a fermentation broth or it can be a extract from the fermentation broth itself, which still contains the cells of the *Eupenicillium crustaceum* species. It is referred herein as the ferment extract or simply the extract.

The ferment extract can be obtained through the fermentation of a strain of *Eupenicillium crustaceum* species in a suitable aqueous culture medium. The fermentation broth is conventionally stirred and aerated to enable the synthesis and secretion of the desired product to the culture medium and this is followed by the isolation and purification of a ferment extract. Fermentation can be carried out in a medium stirred and aerated at a temperature of between 15° C. and 40° C., typically at 25° C., with the medium having a pH between 5 and 9, typically around 7.5, adjusted if necessary during fermentation. The duration of the fermentation is between 2 to 10 days, in one embodiment between 3 to 8 days, in other embodiment, between 4 and 7 days.

The method of isolation and purification of the ferment extract from the fermentation broth can be carried out by the methods known to the person skilled in the art, such as centrifugation, disruption and extraction. For example, in a first step, centrifugation can be used to separate the cells from the strain of *Eupenicillium crustaceum* species from the culture broth; in a second step, disruption can be used to release the intracellular compounds; and in a third step, an extraction of the intracellular compounds can be performed to obtain the ferment extract. The extract will include those intracellular compounds that are soluble in the extraction solvent. The ferment extract can be obtained simply by extraction of the fermentation broth, that is, without centrifugation and disruption steps. However, preferably a disruption step is employed to maximize yield of the desired product.

In the fermentation of the strain of *Eupenicillium crustaceum* species a culture medium containing exogenous sugars, such as and not restricted to, galactose, glucose, mannose, mannitol, amygdalin, cellobiose, maltose, starch, glycogen, lactose, mixtures thereof and/or extracts containing mixtures of these sugars can be used as a carbon source. In one embodiment, an exogenous supply of mannitol of 2 to 40 g/L, or from 3 to 10 g/L can be provided.

The culture medium may comprise additional nitrogen or carbon sources such as yeasts extracts, malt extracts or peptones, with concentrations of each one of these components of 0.1 to 20 g/L, or from 0.5 to 10 g/L.

The culture medium may comprise sea salts. Sea salts are mineral salts at a concentration between 5 and 40 g/L, or between 25 and 35 g/L. In one embodiment, in addition or alternatively to the sea salts, mineral salts are also provided to the fermentation culture medium. These salts are selected among salts which provide the ions $Na^+$, $K^+$, $NH_4^+$, $Ca^{2+}$, $Mg^{2+}$, $PO_4^{3-}$, $SO_4^{2-}$, $Cl^-$, $F^-$, $I^-$, $CO_3^{2-}$, $NO_3^-$, citrates, or trace elements such as Cu, Mn, Mo, Fe, Sr, B, Br, Si, Al, Li, and Zn.

The extraction step is carried out using a solvent such as isopropanol. Other solvents such as ethanol, acetone and ethyl acetate can be used.

The ferment extract from the *Eupenicillium crustaceum* species strain typically contains peptides, free amino acids, carbohydrates and lipids. In one embodiment, the ferment extract comprises relative species percentages of: 31 to 79% of peptides, 1 to 8% of free amino acids, 10 to 27% of carbohydrates, and 15 to 40% of lipids, with the condition that the sum of percentages does not exceed 100%. In another embodiment the ferment extract shows relative species percentages of: 35 to 73% of peptides, 2 to 7% of free amino acids, 12 to 25% of carbohydrates, and 17 to 37% of lipids, with the condition that the sum of percentages does not exceed 100%. In another embodiment, the ferment extract shows relative species percentages of: 39.4 to 65.6% of peptides, 2.2 to 6.4% of free amino acids, 13.3 to 22% of carbohydrates, and 18.8 to 32.8% of lipids, with the condition that the sum of percentages does not exceed 100%. In another embodiment, the ferment extract shows relative species percentages of: 39 to 46% of peptides, 3 to 7% of free amino acids, 21 to 22% of carbohydrates, and 29 to 33% of lipids, with the condition that the sum of percentages does not exceed 100%. These percentages are weight percentages.

Typically, the ferment extract has a molecular weight less than 3,400 Da. This is measured by chromatographic (HPLC) analysis with a size exclusion column TSK gel G2000SWXL, under the conditions detailed in Example 2. The size exclusion column has an internal diameter of 7.8 mm, a length of 30.0 cm, a particle size of 5 mm and a pore size of 125 Å. The eluent was 0.1M buffer phosphate pH 6.7+0.1M $Na_2SO_4$ and elution was kept isocratic at a flow rate of 1 mL/min. The ferment extract from the *Eupenicillium crustaceum* species, shows peaks between 11.5 and 13.5 min, peaks with a Gaussian distribution having a residence time between 10 and 20 minutes.

In an exemplary and preferred embodiment, the strain of *Eupenicillium crustaceum* species is a strain of *Eupenicillium crustaceum* species with deposit number CECT 20901. This strain was deposited on Mar. 20, 2014 at the at the Colección Española de Cultivos Tipo (CECT) (Edificio 3 CUE, Parc Cientific Universitat de Valencia, Catedrático Agustín Escardino 9, 46980 Paterna, Valencia, Spain), an institution legally recognized for said purpose according to the Budapest Treaty on the International Recognition of the Deposit of Microorganisms on Apr. 28, 1977.

In a second aspect, the invention provides for the use of the ferment extract for the cosmetic treatment and/or care of the skin, mucous membranes, hair and/or nails. In particular, it has been found that the ferment extract is particularly effective in the cosmetic treatment and/or care of the skin, including: the depigmentation of or the whitening or the lightening in color of the skin, mucous membranes, hair and/or nails; the depigmentation of or the whitening or the lightening in color of age spots; the depigmentation of or the whitening or the lightening in color of the skin of dark eye circles; the maintenance or improvement of skin luminosity; the alleviation of the symptoms of skin aging; treatment of skin wrinkles, such as periorbital wrinkles; treatment of dark under-eye circles; treatment of puffy eye; treatment of eye bags; the smoothing out of or reduction of skin wrinkles; the reduction in volume of a puffy eye or of eye bags; the maintenance or improvement of skin elasticity; the maintenance or improvement of skin resistance, firmness or tensile strength. It has been found that the ferment extract can promote collagen and elastin synthesis, inhibit degradation of collagen due to the action of collagenase and inhibit degradation of elastin due to the action of elastase. It is believed said ferment extract serves to replenish and maintain collagen and elastin levels in aging skin, thus maintaining and improving skin elasticity, skin resistance and/or skin tensile strength. This leads to more toned and firmer skin which has less of a tendency to sag and/or wrinkle. It has also been found that said ferment extract can inhibit the formation of Advance Glycation End products (AGEs). It is believed that this further adds to the ferment extract's ability to help maintain collagen (collagen Type I) levels in aging skin, and, as a result, maintain skin elasticity. Further, this ability to inhibit the formation of AGEs leads to a decrease in the formation of compounds which along with a decrease in elastin is believed to cause skin dullness, and thus use of this cosmetic active can improve skin luminosity. Thus, in one embodiment of the second aspect of the invention, there is provided the cosmetic use of said ferment extract for the maintenance or improvement of skin elasticity, skin resistance, skin firmness, skin tensile strength and/or skin luminosity. The invention provides said ferment extract for the cosmetic use in the maintenance or improvement of skin elasticity, skin resistance, skin tensile strength and/or skin luminosity, and the cosmetic use of said ferment extract as a skin firming and toning agent and/or a skin brightening agent.

Further, it has been found that the ferment extract of the invention is effective in the smoothing out of or the reduction in size of skin wrinkles, in particular periorbital wrinkles, such as crow's feet. Thus, in one embodiment of the second aspect of the invention, there is provided the cosmetic use of said ferment extract for the treatment of wrinkles. The invention provides said ferment extract for the cosmetic use in the treatment of wrinkles, and the cosmetic use of said ferment extract as a skin anti-wrinkle agent.

It has also been found that the ferment extract of the invention is effective in decreasing the volume of eye bags. It is believed that this is at least in part due to the ferment extract's effectiveness in decreasing vascular permeability (increasing vascular permeability being associated with aging skin) and thus reducing the amount of fluid retained in the skin under the eye. Thus in one embodiment of the second aspect of the invention, there is provided the cosmetic use of said ferment extract for the treatment of eye bags and/or puffy eyes. The invention provides said ferment extract for the cosmetic use in the treatment of eye bags and/or puffy eyes, and the cosmetic use of said ferment extract as an eye bag and/or puffy eye treating agent.

It has also been found that the ferment extract of the invention is effective in the lightening the color or the depigmenting or the whitening of the skin. It is believed that this is in part due to the ferment extract's effectiveness in inhibiting melanin formation in melanocytes, inhibiting tyrosinase activity and/or affecting the expression of genes that are involved in the melanogenic process. Thus, in one embodiment of the second aspect of the invention, there is provided the cosmetic use of said ferment extract for the lightening in color or whitening or depigmentation of skin, mucous membranes, hair and/or nails. The invention provides said ferment extract for the cosmetic use of whitening or lightening in color or depigmentation of skin, and the cosmetic use of said ferment extract as a skin whitening agent or skin color lightening agent or skin depigmentation agent. In particular, the ferment extract is effective in the lightening the color or the depigmenting or the whitening of hyperpigmented skin, for example, age spots. It is believed that this ability to affect age spots is in part due to the ferment extract's effectiveness in the downregulation of EDNRB gene expression and the inhibitory effect in the Wnt signaling pathway in melanocytes (upregulation of the gene DKK1 and downregulation of genes involved in this pathway). Thus in one embodiment of the second aspect of the invention, there is provided the cosmetic use of said ferment extract for the treatment of age spots. The invention provides for said ferment extract for the cosmetic use in the treatment of age spots, and the cosmetic use of said ferment extract as an age spot treating agent. The ferment extract of the invention is also particularly effective in lightening the dark color of the skin in dark eye circles. It is believed that this is in part due to the ferment extract's effectiveness in promoting bilirubin breakdown as well as its ability to affect melanin formation. Thus in one embodiment of the second aspect of the invention, there is provided the cosmetic use of said ferment extract for the treatment of dark eye circles. The invention provides for said ferment extract for the cosmetic use in the treatment of dark eye circles and the cosmetic use of said ferment extract as a dark eye circle treating agent. This skin color lightening ability also contributes to the ferment extract's ability to maintain and/or improve skin luminosity.

In one embodiment of the second aspect of the invention, there is provided the use of the ferment extract of the invention for the alleviation of the symptoms or signs of skin aging. Thus, the invention provides said ferment extract for the cosmetic use in the alleviation of the symptoms of skin aging and the cosmetic use of said ferment extract as a skin anti-aging agent. The symptoms or signs of skin aging include: the appearance of skin wrinkles, dark eye circles, age spots, puffy eyes and/or eye bags, the dulling of the skin, loss of skin elasticity, skin resistance, skin firmness and/or skin tensile strength. Thus in this embodiment, the cosmetic treatment and/or care includes: the treatment of skin wrinkles, dark eye circles, age spots, puffy eyes and/or eye bags; the smoothing out or reduction in size of skin wrinkles; the reduction in volume of puffy eyes and/or eye bags; the lightening in color of the skin of dark eye circles; the lightening in color of age spots; the maintenance or improvement of skin elasticity, skin luminosity, skin resistance, skin firmness and/or skin tensile strength. In one embodiment, the cosmetic treatment and/or care is the lightening, whitening or depigmentation of the skin and includes the lightening in color of the skin of dark eye circles and/or age spots and/or the maintenance or improvement of skin luminosity. In one embodiment the cosmetic treatment and/or care is the treatment of the skin around the eye area and includes the treatment of skin wrinkles, dark eye circles, puffy eyes and/or eye bags.

In one embodiment of the invention, the cosmetic treatment and/or care of the skin, mucous membranes, hair and/or nails is for skin which is most exposed to the environment such as facial skin, the skin of the hands and forearms, the décolletage and the legs. In one embodiment of the invention, where the cosmetic treatment and/or care of the skin, mucous membranes, hair and/or nails is for the lightening in color, whitening or depigmenting, the treatment and/or care is for skin for which a lighter color is cosmetically desired by an individual, such as hyperpigmented skin such as age spots or skin which is naturally darker due to a high melanin content such as the skin of the nipple.

In one embodiment, the cosmetic treatment and/or care is for an individual that is Caucasian or Asian. In one embodiment, the cosmetic treatment and/or care is for an individual that is over the age of 20.

According to the third aspect of the invention, there is provided a cosmetic composition which comprises a cosmetically effective quantity of the ferment extract from a strain of *Eupenicillium crustaceum* species and at least one cosmetically acceptable excipient, adjuvant and/or ingredient. The ferment extract is as described in the first aspect of the invention. Said compositions can be prepared by the conventional methods known by the persons skilled in the art ["*Harry's Cosmeticology*", Seventh edition, (1982), Wilkinson J. B., Moore R. J., ed. Longman House, Essex, GB].

The cosmetically effective quantity of the ferment extract in the composition of the invention, as well as its dosage, will depend on numerous factors, which can include age, condition of the patient, the nature or severity of the signs of skin aging, the darkness of the skin to be treated and/or cared for, the route and frequency of administration of the extract.

"Cosmetically effective quantity" is understood to be a non-toxic but sufficient quantity of the ferment extract to provide the desired effect. The ferment extract of the invention is used at concentrations to achieve the desired cosmetic effect and these include, based on the extract dry weight respect to the total weight of the composition, from 0.0000000001 wt % to 20 wt % or from 0.00000001 wt % to 10 wt %, or from 0.000001 wt % to 5 wt %, or from 0.000001 wt % or 0.00005 to 1 wt %.

The ferment extract of the invention can be incorporated into cosmetic delivery systems and/or sustained release systems.

The term "delivery systems" relates to a diluent, adjuvant, vehicle or additives with which the extract of the invention is administered. These cosmetic carriers can be liquids, such as water, oils or surfactants, including those of petroleum, animal, plant or synthetic origin, such as and not restricted to, peanut oil, soybean oil, mineral oil, sesame oil, castor oil, polysorbates, sorbitan esters, ether sulfates, sulfates, betaines, glycosides, maltosides, fatty alcohols, nonoxynols, poloxamers, polyoxyethylenes, polyethylene glycols, dextrose, glycerol, digitonin and similar. A person skilled in the art is aware of the diluents, adjuvants or additives that can be used in the different delivery systems in which the ferment extract of the invention can be administered.

The term "sustained release" is used in a conventional sense to describe a delivery system which provides the gradual release of a compound over a period of time. In one embodiment, the delivery system provides relatively constant compound release levels over a period of time.

Examples of delivery or sustained release systems include liposomes, mixed liposomes, oleosomes, niosomes, ethosomes, milliparticles, microparticles, nanoparticles and solid lipid nanoparticles, nanostructured lipid carriers, sponges, cyclodextrins, vesicles, micelles, mixed micelles of surfactants, surfactant-phospholipid mixed micelles, millispheres, microspheres and nanospheres, liposheres, millicapsules, microcapsules and nanocapsules, as well as microemulsions and nanoemulsions, which can be added to achieve a greater penetration of the active ingredient of the invention. In one embodiment, the delivery or sustained release systems are chosen from liposomes, surfactant-phospholipid mixed micelles and microemulsions, water-in-oil microemulsions with an internal reverse micelle structure, and microemulsions containing nanocapsules.

The sustained release system can be prepared by methods known in the prior art, and the compositions which contain them can be administered, for example, by topical or transdermal administration, including adhesive patches, non-adhesive patches, occlusive patches and microelectric patches. In one embodiment, the sustained release system should release a relatively constant quantity of the extract of the invention. The amount of extract contained in the sustained release system will depend, for example, on where the composition is to be administered, the kinetics and duration of the release of the extract of the invention, as well as the nature of the condition, disorder and/or disease to be treated or prevented.

The composition containing the ferment extract of this invention can also be adsorbed on solid organic polymers or solid mineral supports, such as and not restricted to, talc, bentonite, silica, starch or maltodextrin among others.

The compositions containing the ferment extract can also be incorporated into fabrics, non-woven fabrics or medical devices which are in direct contact with the skin, thus releasing the extract of the invention whether by biodegradation of the binding system to the fabric, non-woven fabric or medical device, or due to the friction between them and the body, due to body moisture, the skin's pH or body temperature. Furthermore, the extract of the invention can be incorporated into the fabrics and non-woven fabrics used in the manufacture of garments that are in direct contact with the body.

Examples of fabrics, non-woven fabrics, garments, medical devices and means for immobilizing the compounds to them, among which are the delivery systems and/or the sustained release systems described above, can be found in the literature and are known in the prior art [Schaab C. K. (1986) HAPPI May 1986; Nelson G., "*Application of microencapsulation in textiles*", (2002), Int. J. Pharm., 242(1-2), 55-62; "*Biofunctional Textiles and the Skin*" (2006) Curr. Probl. Dermatol. v.33, Hipler U. C. and Elsner P., eds. S. Karger A G, Basel, Switzerland; Malcolm R. K. et al., "*Controlled release of a model antibacterial drug from a novel self-lubricating silicone biomaterial*", (2004), J. Cont. Release, 97(2), 313-320]. The preferred fabrics, non-woven fabrics, garments and medical devices are bandages, gauzes, t-shirts, socks, tights, underwear, girdles, gloves, diapers, sanitary napkins, dressings, bedspreads, wipes, adhesive patches, non-adhesive patches, occlusive patches, microelectric patches and/or face masks.

The cosmetic compositions containing the ferment extract of this invention can be used in different types of compositions of topical or transdermal application, optionally including cosmetically acceptable excipients necessary for formulating the desired administration form.

The cosmetic compositions of the invention can be for topical or transdermal application and can be produced in any solid, liquid or semi-solid formulation, such as and not restricted to, creams, multiple emulsions such as and not restricted to, oil and/or silicone in water emulsions, water-in-oil and/or silicone emulsions, water/oil/water or water/silicone/water type emulsions, and oil/water/oil or silicone/water/silicone type emulsions, anhydrous compositions, aqueous dispersions, oils, milks, balsams, foams, lotions, gels, cream gels, hydroalcoholic solutions, hydroglycolic solutions, hydrogels, liniments, sera, soaps, shampoos, conditioners, serums, polysaccharide films, ointments, mousses, pomades, powders, bars, pencils and sprays or aerosols (sprays), including leave-on and rinse-off formulations. These topical or transdermal application formulations can be incorporated, using techniques known by the person skilled in the art, into different types of solid accessories such as and not restricted to, bandages, gauzes, t-shirts, socks, tights, underwear, girdles, gloves, diapers, sanitary napkins, dressings, bedspreads, wipes, adhesive patches, non-adhesive patches, occlusive patches, microelectric patches or face masks, or they can be incorporated into different make-up products such as make-up foundation, such as fluid foundations and compact foundations, make-up removal lotions, make-up removal milks, under-eye concealers, eye shadows, lipsticks, lip protectors, lip gloss and powders, among others.

The cosmetic compositions of the invention may include agents which increase the percutaneous absorption of the compounds of this invention, for example and not restricted to, dimethyl sulfoxide, dimethylacetamide, dimethylformamide, surfactants, azone (1-dodecylazacycloheptane-2-one), alcohol, urea, ethoxydiglycol, acetone, propylene glycol or polyethylene glycol, among others. Furthermore, the cosmetic or dermopharmaceutical compositions of this invention can be applied to local areas to be treated by means of iontophoresis, sonophoresis, electroporation, microelectric patches, mechanical pressure, osmotic pressure gradient, occlusive cure, microinjections or needle-free injections by means of pressure, such as injections by oxygen pressure, or any combination thereof, to achieve a greater penetration of the extract of the invention. The application area will be determined by the nature of the condition, disorder and/or disease to be treated and/or prevented.

Among the cosmetically acceptable excipients, adjuvants and/or ingredients contained in the cosmetic compositions described in this invention are additional ingredients commonly used in cosmetic compositions such as and not restricted to, agents which diminish the sebum production, anti-seborrheic agents, mattifying agents, anti-acne agents, agents stimulating the synthesis of dermal or epidermal macromolecules and/or capable of inhibiting or preventing their degradation, other collagen synthesis-stimulating agents, other elastin synthesis-stimulation agents, decorin synthesis-stimulation agents, laminin synthesis-stimulation agents, defensin synthesis-stimulating agents, chaperone synthesis-stimulating agents, cAMP synthesis-stimulating agents, agents that modulate AQP-3, agents that modulate aquaporin synthesis, proteins from the aquaporin family, hyaluronic acid synthesis-stimulating agents, glycosaminoglycan synthesis-stimulating agents, fibronectin synthesis-stimulating agents, sirtuin synthesis-stimulating agents, heat shock proteins, heat shock protein synthesis-stimulating agents, agents which inhibit neuronal exocytosis, other anticholinergic agents, agents which inhibit muscular contraction, other anti-aging agents, other anti-wrinkle agents, antiperspirant agents, anti-inflammatory agents and/or analgesics, anti-itching agents, calming agents, anesthetic agents, inhibitors of acetylcholine-receptor aggregation, agents that inhibit acetylcholinesterase, skin relaxant agents, other melanin synthesis inhibiting agents, whitening or depigmenting agents, NO-synthase inhibiting agents, 5α-reductase inhibiting agents, lysyl- and/or prolyl hydroxylase inhibiting agents, antioxidants, free radical scavengers and/or agents against atmospheric pollution, reactive carbonyl species scavengers, anti-glycation agents, antihistamine agents, antiviral agents, antiparasitic agents, emulsifiers, emollients, organic solvents, liquid propellants, skin conditioners, humectants, substances that retain moisture, alpha hydroxy acids, beta hydroxy acids, moisturizers, epidermal hydrolytic enzymes, vitamins, amino acids, proteins, pigments or colorants, dyes, biopolymers, gelling polymers, thickeners, surfactants, softening agents, emulsifiers, binding agents, preservatives, agents able to reduce or treat the bags under the eyes, exfoliating agents, keratolytic agents, desquamating agents, antimicrobial agents, antifungal agents, fungistatic agents, bactericidal agents, bacteriostatic agents, agents stimulating the synthesis of lipids and components of the stratum corneum, ceramides, fatty acids, other agents that inhibit collagen degradation, agents that inhibit matrix metalloproteinases, other agents that inhibit elastin degradation, agents that inhibit serine proteases such as kallikreins, leukocyte elastase or cathepsin G, agents stimulating fibroblast proliferation, agents stimulating keratinocyte proliferation, agents stimulating adipocyte proliferation, agents stimulating melanocyte proliferation, agents stimulating keratinocyte differentiation, agents stimulating or delaying adipocyte differentiation, antihyperkeratosis agents, comedolytic agents, anti-psoriasis agents, DNA repair agents, DNA protecting agents, stem cell protecting agents, stabilizers, agents for the treatment and/or care of sensitive skin, firming agents, anti-stretch mark agents, binding agents, lipolytic agents or agents stimulating lipolysis, adipogenic agents, agents modulating PGC-1α expression, agents modulating the activity of PPARγ, agents which increase or reduce the triglyceride content of adipocytes, anti-cellulite agents, agents which inhibit the activity of PAR-2, agents stimulating healing, coadjuvant healing agents, agents stimulating reepithelialization, coadjuvant reepithelialization agents, cytokine growth factors, agents acting on capillary circulation and/or microcirculation, agents stimulating angiogenesis, agents that inhibit vascular permeability, venotonic agents, agents acting on cell metabolism, agents which improve dermal-epidermal junction, agents inducing hair growth, hair growth inhibiting or retardant agents, hair loss retardant agents, preservatives, perfumes, odor absorbents and/or body odor masking deodorants, chelating agents, plant extracts, essential oils, marine extracts, agents obtained from a biotechnological process, mineral salts, cell extracts, sunscreens and organic or mineral photoprotective agents active against ultraviolet A and/or B rays and/or infrared A rays, or mixtures thereof, provided that they are physically and chemically compatible with the rest of components in the composition and particularly with the ferment extract produced by the strain of the *Eupenicillium crustaceum* species. Likewise, the nature of these additional ingredients should not unacceptably alter the benefits of the extract of this invention. The nature of these additional ingredients can be synthetic or natural, such as plant extracts, or come from a biotechnological process, or from a combination of a synthetic process and a biotechnological process. Additional examples can be found in *CTFA International Cosmetic Ingredient Dictionary & Handbook,* 12th Edition (2008). In the context of this invention, biotechnological process is understood to be any process to produce the active ingredient, or part of it, in an organism, or in part of it.

In one embodiment, the cosmetic composition of the invention contains:

between 0.0000000001% (in weight) and 20% (in weight) of the ferment extract from a strain of *Eupenicillium crustaceum* species;

between 0.1% (in weight) and 20% (in weight) of an humectant selected from the group of (INCI Names) Glycerin, Propylene Glycol, Butylene Glycol, Pentylene Glycol, Caprylyl Glycol, Lactic Acid, Urea, Sodium Hyaluronate;

between 0.1% (in weight) and 20% (in weight) of an emollient or skin conditioning selected from the group of (INCI Names) Dimethicone, Glyceryl Stearate, Caprylic/Capric Triglyceride, Cetearyl Alcohol, Lecithin, C12-15 Alkyl Benzoate, Squalane, Lanolin, Behenyl Alcohol, Tocopheryl Acetate, Panthenol, Butyrospermum Parkii Butter, Retinyl Palmitate, Retinol;

between 0.1% (in weight) and 20% (in weight) of a surfactant selected from the group of (INCI Names) Xanthan Gum, Sodium Laureth Sulfate, Stearic Acid, Polysorbate 20, Polysorbate 80, Stearyl Alcohol, Cetyl Alcohol, Steareth-2, Ceteareth-20, Cocamidopropyl Betaine.

The composition can further comprise an agent which diminishes sebum production, an anti-seborrheic agent, a mattifying agent and/or an anti-acne agent, for example and not restricted to, an agent selected from the group formed by Mat-XS Clinical [INCI: Sarcosine, Xanthan gum], Mat-XS Bright™ [INCI: *Orthosiphon Stamineus* Leaf Extract, Maltodextrin, Xanthan Gum], Betapur™ [INCI: *Peumus Boldus* Leaf Extract, Xanthan Gum] or Neurobiox™ [INCI: *Achillea Millefolium* Extract, Xanthan Gum] marketed by BASF, Evermat™ [INCI: Enantia Chlorantha Bark Extract, Oleanolic Acid], Ac.net™ [INCI: Butylene Glycol, Peg-60 Almond Glycerides, Caprylyl Glycol, Glycerin, Carbomer, Nordihydroguaiaretic Acid, Oleanolic Acid] or Sebuless™ [INCI: Maltodextrin, Syringa Vulgaris (Lilac) Extract] marketed by Sederma/Croda, Phytessence™ Purple Ginseng [INCI: Glycerin or Polygonum Bistorta Root Extract] marketed by Crodarom, P-Refinyl® [INCI: Lens Esculenta (Lentil) Seed Extract], marketed by Silab, EPS Seamat™ [INCI: Planktonic Exopolysaccharide-5, Phenoxyethanol] or Epidermist™ 4.0 [INCI: Plankton Extract], marketed by Codif, Seborami® [INCI: Sisymbrium Officinale Extract, Arctium Lappa Root Extract, Citric Acid, Glycolic Acid, Zinc PCA, *Sclerotium* Gum] marketed by Alban Muller, Poreaway™ [INCI: Pistacia Lentiscus Gum/Pistacia Lentiscus (Mastic) Gum, Lecithin] marketed by Mibelle, Citrustem™ [INCI: Xanthan Gum, Sodium Benzoate, Gluconolactone, Calcium Gluconate] or Affipore™ [INCI: Barosma Betulina Leaf Extract, Citric Acid], marketed by Provital, Sweetone® [INCI: Saccharide Hydrolysate, Maltodextrin], marketed by Laboratories Expanscience, Seboxyl® [INCI: Ribes Nigrum (Black Currant) Leaf Extract, *Rubus Idaeus* (Raspberry) Leaf Extract] or Saniskin® [INCI: Polygonum Cuspidatum Root Extract, Myristyl Alcohol], marketed by Solabia, Alpaflor® Alp-Sebum [INCI: Epilobium Fleischeri Extract, Citric Acid, Potassium Sorbate] or Regu®-Seb [INCI: Argania Spinosa Kernel Extract, *Serenoa Serrulata* Fruit Extract, *Sesamum Indicum* (Sesame) Seed Extract], marketed by DSM, Bodyfensine® [INCI: Acetyl Dipeptide-3 Aminohexanoate], Matmarine™ [INCI: Pseudoalteromonas Ferment Extract], marketed by Lipotec/Lubrizol, Dermaclarine™ [INCI: Hydrolyzed Egg Protein (and) Protease] marketed by Aqua Bio Technology, Linumine™ [INCI: Linum Usitatissimum (Linseed) Seed Extract], marketed by Lucas Meyer, Granactive™ Acne [INCI: *Oryza Sativa* (Rice) Bran Extract, Boswellia Serrata Extract, Honey Extract, Oligopeptide-10], marketed by Evonik, Sepicontrol™ A5 [INCI: Capryloyl Glycine, Sarcosine, Cinnamomum Zeylanicum Bark Extract], marketed by Seppic, Sympeptide™ 380 [INCI: Myristoyl Hexapeptide-23] marketed by Symrise, or Sebaryl™ [INCI: Niacinamide, Yeast Extract, Aesculus Hippocastanum (Horse Chestnut) Seed Extract, Ammonium Glycyrrhizate, Panthenol, Propylene Glycol, Zinc Gluconate, Caffeine, Biotin], marketed by Laboratoires Serobiologiques/Cognis/BASF, among others.

The composition can further comprise an additional anti-wrinkle and/or anti-aging agent selected, for example and not restricted to, from the group formed by the extracts or hydrolyzed extracts of *Vitis vinifera, Rosa canina, Curcuma longa, Theobroma cacao, Ginkgo biloba, Leontopodium alpinum* or *Dunaliella salina* among others, Matrixyl® [INCI: Palm itoyl Pentapeptide-4], Matrixyl® 3000® [INCI: Palm itoyl Tetrapeptide-7, Palm itoyl Oligopeptide], Matrixyl® Synthe'6™ [INCI: Glycerin, Water, Hydroxypropyl Cyclodextrin, Palm itoyl Tripeptide-38], Essenskin™ [INCI: calcium hydroxymethionine], Renovage [INCI: teprenone], Resistem™ [INCI: Globularia Cordifolia Ferment], Beautifeye [INCI: Albizia Julibrissin Bark Extract, Darutoside], Meiritage [INCI: Astragalus Membranaceus Root Extract, *Atractyloides* Macrocephala Root Extract, *Bupleurum* Falcatum Root Extract], Senestem [INCI: Plantago Lanceolata Leaf Extract], Beautifeye™ [INCI: ALbizia Julibrissin Bark Extract], Venuceane [INCI: Thermus Thermophillus Ferment] or Dermaxyl® [INCI: Palmitoyl Oligopeptide] marketed by Sederma/Croda, Vialox® [INCI: Pentapeptide-3], Syn®-Ake® [INCI: Dipeptide Diaminobutyroyl Benzylamide Diacetate], Syn®-Coll [INCI: Palmitoyl Tripeptide-5], Phytaluronate [INCI: Locust Bean (*Ceratonia siliqua*) Gum], Regu®-Scence [INCI: Asparagus Officinalis Stem Extract, Sodium Benzoate, Potassium Sorbate, Gluconolactone, Calcium Gluconate], Syn®-TC[INCI: Tetradecyl Aminobutyroylvalylaminobutyric Urea Trifluoroacetate, Palmitoyl Tripeptide-5, Palmitoyl Dipeptide-5 Diaminobutyroyl Hydroxythreonine] or Preregen® [INCI: *Glycine soja* (Soybean) Protein, Oxido Reductases] marketed by Pentapharm/DSM, Myoxinol™ [INCI: Hydrolyzed *Hibiscus esculentus* Extract], Syniorage™ [INCI: Acetyl Tetrapeptide-11], Dermican™ [INCI: Acetyl Tetrapeptide-9], Shadownyl™ [INCI: Algae Extract, Hexylene Glycol, Caprylyl Glycol, Xanthan Gum] or DN AGE™ LS [INCI: *Cassia alata* leaf Extract] marketed by Laboratoires Sérobiologiques/Cognis/BASF, Algisum C® [INCI: Methylsilanol Mannuronate], Exage™ [INCI: Imidazolylethyl Diaminopropanamide] or Hydroxyprolisilane CN® [INCI: Methylsilanol Hydroxyproline Aspartate] marketed by Exsymol, Argireline® [INCI: Acetyl Hexapeptide-8], SNAP-7 [INCI: Acetyl Heptapeptide-4], SNAP-8 [INCI: Acetyl Octapeptide-3], Serilesine® [INCI: Hexapeptide-10], Leuphasyl® [INCI: Pentapeptide-18], Inyline® [INCI: Acetyl Hexapeptide-30], Aldenine® [INCI: Hydrolyzed Wheat Protein, Hydrolyzed Soy Protein, Tripeptide-1], Preventhelia® [INCI: Diaminopropionoyl Tripeptide-33], Decorinyl® [INCI: Tripeptide-10 Citrulline], Decorinol® [INCI: Tripeptide-9 Citrulline], Trylagen® [INCI: Pseudoalteromonas Ferment Extract, Hydrolyzed Wheat Protein, Hydrolyzed Soy Protein, Tripeptide-10 Citrulline, Tripeptide-1], Eyeseryl® [INCI: Acetyl Tetrapeptide-5], Peptide AC29 [INCI: Acetyl Tripeptide-30 Citrulline], Relistase® [INCI: Acetylarginyltriptophyl Diphenylglycine], Thermostressine® [INCI: Acetyl Tetrapeptide-22], Lipochroman™ [INCI: Dimethylmethoxy Chromanol], Chromabright® [INCI: Dimethylmethoxy Chromanyl Palm itate], Antarcticine® [INCI: Pseudoalteromonas Ferment Extract], dGlyage® [INCI: Lysine HCl, Lecithin, Tripeptide-9 Citrulline], Vilastene™ [INCI: Lysine HCl, Lecithin, Tripeptide-10 Citrulline], Hyadisine® [INCI: Pseudoalteromonas Ferment Extract], Hyanify™ [INCI: Saccharide Isomerate], Diffuporine® [INCI: Acetyl Hexapeptide-37], Silusyne® [INCI: Soybean (*Glycine Soja*) Oil, Sorbitan Sesquioleate, Isohexadecane, Sodium Hyaluronate, Lauryldimonium Hydroxypropyl Hydrolyzed Soy Protein, Acetyl Hexapeptide-39], Adifyline® [INCI: Acetyl Hexapeptide-38], Uplevity™ [INCI: Acetyl Tetrapeptide-2], Juveleven™ [INCI: Acetyl Hexapeptide-51 Amide] or Telangyn™ [INCI:

Acetyl Tetrapeptide-40] marketed by Lipotec/Lubrizol, Kollaren® [INCI: Tripeptide-1, Dextran] marketed by Institut Europeen de Biologie Cellulaire, Collaxyl® IS [INCI: Hexapeptide-9], Laminixyl IS™ [INCI: Heptapeptide], Orsirtine™ GL [INCI: *Oryza sativa* (Rice) Extract], D'Orientine™ IS [INCI: *Phoenix dactylifera* (Date) Seed Extract], Phytoquintescine™ [INCI: Einkorn (*Triticum monococcum*) Extract], Peptide Q10™ [INCI: Pentapeptide-34 Trifluoroacetate], Telosense [INCI: Hydrolyzed Yeast Protein, Hydrolyzed Soy Protein] or Quintescine™ IS [INCI: Dipeptide-4] marketed by Vincience/ISP/Ashland, BONT-L-Peptide [INCI: Palmitoyl Hexapeptide-19] marketed by Infinitec Activos, Deepaline™ PVB [INCI: Palmitoyl hydrolyzed Wheat Protein] or Sepilift® DPHP [INCI: Dipalmitoyl Hydroxyproline] marketed by Seppic, Gatuline® Expression [INCI: *Acmella oleracea* Extract], Gatuline® In-Tense [INCI: *Spilanthes acmella* Flower Extract] or Gatuline® Age Defense 2 [INCI: *Juglans regia* (Walnut) Seed Extract] marketed by Gattefossé, Thalassine™ [INCI: Algae Extract] marketed by Biotechmarine, ChroNOline™ [INCI: Caprooyl Tetrapeptide-3] or Thymulen®4 [INCI: Acetyl Tetrapeptide-2] marketed by Atrium/Unipex Innovations, EquiStat™ [INCI: *Pyrus malus* Fruit Extract, *Glycine soja* Seed Extract] or Juvenesce™ [INCI: Ethoxydiglicol and Caprylic Triglyceride, Retinol, Ursolic Acid, Phytonadione, Ilomastat], Epigenist™ [INCI: Voandzeia Subterranea Seed Extract], LOX-AGE™ [INCI: Cichorium Intybus (Chicory) Leaf Extract] marketed by Coletica/Engelhard/BASF, Ameliox™ [INCI: Carnosine, Tocopherol, *Silybum marianum* Fruit Extract], PhytoCellTec™™ Symphytum [INCI: Isomalt, Symphytum Officinale Root Cell Culture, Lecithin, Sodium Benzoate], Snow Algae Powder [INCI: Chlamydocapsa Extract, Maltodextrin, Lecithin], DermCom™ [INCI: Acacia Senegal Gum, Crocus Chrysanthus Bulb Extract], AnaGain™ [INCI: *Pisum Sativum* (Pea), Sprout Extract] or PhytoCellTec™ Malus Domestica [INCI: *Malus domestica* Fruit Cell Culture] marketed by Mibelle Biochemistry, Bioxilift [INCI: *Pimpinella anisum* Extract], Vitagenyl® [INCI: *Prunus Persica* (Peach) Leaf Extract] or SMS Anti-Wrinkle® [INCI: *Annona squamosa* Seed Extract] marketed by Silab, Symvital® AgeRepair [INCI: Zingiber Officinale (Ginger) Root Extract] marketed by Symrise, Citrustem [INCI: Xanthan Gum, Sodium Benzoate, Gluconolactone, Calcium Gluconate], Melavoid™ [INCI: Boerhavia Diffusa Root Extract], Darkout™ [INCI: Hypoxis Rooperi Rhizome Extract, Caesalpinia Spinosa Gum] or Linefill™ [INCI: Dimethyl Isosorbide, *Sesamum Indicum* (Sesame) Seed Extract] marketed by Provital, Adipofill'in™ [INCI: Ornithine, Phospholipids, Glycolipids], Elix-IR™ [INCI: Polygonum Aviculare Extract] or Progeline™ [INCI: Trifluoroacetyl Tripeptide-2] marketed by Lucas Meyer, Amiperfect™ [INCI: Gaultheria Procumbens (Wintergreen) Leaf Extract] or Repulpami ER™ [INCI: Adansonia Digitata Pulp Extract, *Hibiscus Sabdariffa* Flower Extract] marketed by Alban Muller, Celloxyl® [INCI: Uapaca Bojeri Leaf Extract] or Resistress® [INCI: Sophora Japonica Flower Extract] marketed by Solabia, Actiporine 8G™ [INCI: Jania Rubens Extract] or EPS Seafill™ [INCI: Plankton Extract], Lakesis™ [INCI: Pistacia Lentiscus (Mastic) Gum] marketed by Codif, Novhyal® Biotech G [INCI: Disodium Acetyl Glucosamine Phosphate] or Rubixyl® [INCI: Hexapeptide-47] marketed by Induchem, antagonists of the $Ca^{2+}$ channel such as and not restricted to, alverine, manganese or magnesium salts, certain secondary or tertiary amines, retinol and its derivatives, idebenone and its derivatives, Coenzyme Q10 and its derivatives, boswellic acid and its derivatives, GHK and its derivatives and/or salts, carnosine and its derivatives, DNA repair enzymes such as and not restricted to, photolyase or T4 endonuclease V, or chloride channel agonists among others, and/or mixtures thereof.

The composition can further comprise an anti-inflammatory agent and/or analgesic selected, for example and not restricted to, from the group formed by extract of madecassoside, extract of echinacea, amaranth seed oil, sandal wood oil, extract of peach tree leaf, extract of *Aloe vera, Arnica montana, Artemisia vulgaris, Asarum maximum, Calendula officinalis, Capsicum, Centipeda cunninghamii, Chamomilla recutita, Crinum asiaticum, Hamamelis virginiana, Harpagophytum procumbens, Hypericum perforatum, Lilium candidum, Malva sylvestris, Melaleuca alternifolia, Origanum majorana, Origanum vulgare, Prunus laurocerasus, Rosmarinus officinalis, Salix alba, Silybum marianum, Tanacetum parthenium, Thymus vulgaris, Uncaria guianensis* or *Vaccinum myrtillus*, omega-3 and omega-6 fatty acids, Neutrazen™ [INCI: Water, Butylene Glycol, Dextran, Palmitoyl Tripeptide-8] marketed by Atrium Innovations/Unipex Group, Delisens™ [proposed INCI: Acetyl Hexapeptide-46] marketed by Lipotec/Lubrizol, Meliprene® [INCI: Dextran, Acetyl Heptapeptide-1] marketed by Institut Européen de Biologie Cellulaire/Unipex Group, Skinasensyl™ [INCI: Acetyl Tetrapeptide-15] or Anasensyl™ [INCI: Mannitol, Ammonium Glycyrrhizate, Caffeine, Hippocastanum (Horse Chestnut) Extract], Shawdonyl™ [INCI: Algae Extract, Hexylene Glycol, Caprylyl Glycol, Xanthan Gum] marketed by Laboratoires Serobiologiques/Cognis/BASF, MAXnolia™ [INCI: Magnolia Officinalis Bark Extract, Vitis Vinifera/Vitis Vinifera (Grape) Seed Extract, Tocopherol], CM-Naringenin-Chalcone [INCI: Tetrasodium Tetracarboxymethyl Naringeninchalcone] marketed by Mibelle, Unisooth™ [INCI: Propyl Gallate, Gallyl Glucoside, Epigallocatechin Galletyl Glucoside] marketed by Induchem, Calmosensine™ [INCI: Acetyl Dipeptide-1] marketed by Sederma/Croda, coenzyme Q10 or alkyl glyceryl ethers.

The composition can further comprise an additional firming and/or redensifying and/or restructuring agent selected, for example and not restricted to, from the group formed by extracts of *Malpighia puniciftolia, Cynara scolymus, Gossypium herbaceum, Aloe Barbadensis, Panicum miliaceum, Morus nigra, Sesamum indicum, Glycine soja, Triticum vulgare*, Pronalen® Refirming HSC [INCI: *Triticum Vulgare, Silybum Marianum, Glycine Soy, Equisetum Arvense, Alchemilla Vulgaris, Medicago Sativa, Raphanus Sativus*], Lipout™ [INCI: Plankton Extract] or Polyplant® Refirming [INCI: Coneflower, Asiatic *Centella*, Fucus, Fenugreek] marketed by Provital, Lanablue® [INCI: Sorbitol, Algae Extract] marketed by Atrium Biotechnologies/Unipex Innovations, Pepha®-Nutrix [INCI: Natural Nutrition Factor] marketed by Pentapharm/DSM, plant extracts containing isoflavones, Biopeptide EL™ [INCI: Palmitoyl Oligopeptide], Biopeptide CL™ [INCI: Palmitoyl Oligopeptide], Vexel® [INCI: Water (Aqua), Propylene Glycol, Lecithin, Caffeine, Palm itoyl Carnitine], Matrixyl® [INCI: Palm itoyl Pentapeptide-3], Matrixyl® 3000 [INCI: Palmitoyl Tetrapeptide-3, Palm itoyl Oligopeptide] or Bio-Bustyl™ [INCI: Glyceryl Polymethacrylate, Rahnella Soy Protein Ferment, Water (Aqua), Propylene Glycol, Glycerin, PEG-8, Palmitoyl Oligopeptide] marketed by Sederma/Croda, Dermosaccharides® HC [INCI: Glycerin, Water (Aqua), Glycosaminoglycans, Glycogen], Aglycal® [INCI: Mannitol, Cyclodextrin, Glycogen, *Arctostaphylos Uva Ursi* Leaf Extract], Cytokinol® LS [INCI: Hydrolyzed Casein, Hydrolyzed Yeast Protein, Lysine HCl] or Firmiderm® LS9120

[INCI: Terminalia Catappa Leaf Extract, *Sambucus Nigra* Flower Extract, PVP, Tannic Acid] marketed by Laboratoires Serobiologiques/Cognis/BASF, Liftline® [INCI: Hydrolyzed Wheat Protein], Raffermine® [INCI: Hydrolyzed Soy Flour] or Ridulisse C® [Hydrolyzed Soy Protein] marketed by Silab, Serilesine® [INCI: Hexapeptide-10], Decorinyl™ [INCI: Tripeptide-10 Citrulline], Trylagen® [INCI: Pseudoalteromonas Ferment Extract, Hydrolyzed Wheat Protein, Hydrolyzed Soy Protein, Tripeptide-10 Citrulline, Tripeptide-1], Silusyne™ [INCI: Soybean (*Glycine Soja*) Oil, Sorbitan Sesquioleate, Isohexadecane, Sodium Hyaluronate, Lauryldimonium Hydroxypropyl Hydrolyzed Soy Protein, Acetyl Hexapeptide-39] or Adifyline™ [INCI: Acetyl Hexapeptide-38] marketed by Lipotec/Lubrizol, Ursolisome® [INCI: Lecithin, Ursolic Acid, Atelocollagen, Xanthan Gum, Sodium Chondroitin Sulfate], Eperuline [INCI: Maltodextrin, Eperua Falcata Bark Extract] or Collalift® [INCI: Hydrolyzed Malt Extract] marketed by Coletica/Engelhard/BASF, Syn®-Coll [INCI: Palmitoyl Tripeptide-5] marketed by Pentapharm/DSM, Hydriame® [INCI: Water (Aqua), Glycosaminoglycans, *Sclerotium* Gum] marketed by Atrium Biotechnologies/Unipex Innovations, Sphingokine® NP [INCI: Caprooyl Phytosphingosine] marketed by Evonik, Body3 Complex™ [INCI: Bentonite, Butyrospermum Parkii (Shea) Nut Extract, Persea Gratissima (Avocado) Fruit Extract] marketed by Lucas Meyer, Prosynergen™ DF [INCI: *Lactobacillus*/Ulkenia Amoeboidea Ferment Extract Filtrate] marketed by Lonza or IP2000™ [INCI: Dextran, Trifluoroacetyl Tripeptide-2] marketed by Institut Europeen de Biologie Cellulaire/Unipex Innovations, among others.

The composition can further comprise an agent that reduces the triglyceride content of adipocytes, an agent that delays adipocyte differentiation, an anti-cellulite agent, a lipolytic agent, a venotonic agent, an agent inhibiting PGC-1α expression or an agent inhibiting the activity of PPARγ. Such agents can be selected, for example and not restricted to extracts or hydrolyzed extracts of *Alchemffla vulgaris, Angelica sinensis, Armeniacae* sp.*, Arnica montana* L, *Atractyloides platyicodon,* bamboo*, Betula alba, Bupleurum chinensis, Calendula officinalis,* cangzhu*, Cecropia obtusifolia, Celosia cristata, Centella asiatica, Chenopodium quinoa, Chrysanthellum indicum, Cimifuga racemosa, Citrus aurantium amara, Cnicus benedictus, Coffea arabica, Cola nitida, Coleus barbatus, Coleus blumei, Coleus esquirolii, Coleus forskohlii, Coleus scutellarioides, Coleus* sp.*, Coleus xanthanthus, Commiphora myrrha, Crithmum maritimum, Cuminum cyminum, Dioscorea collettii, Dioscorea villosa, Eugenia caryophyllus, Filipendula ulmaria* L*, Foeniculum vulgare, Fucus vesiculosus, Gelidium Cartilagineum, Ginkgo biloba, ginkgo biloba, Glycine max, Glycyrrhiza glabra, Hedera helix* (ivy extract)*, Hibiscus sabdariffa, Hordeum vulgare, Humulus lupulus, Hypericum perforatum, Ilex paraguariensis, Kigelia africana, Laminaria digitata, Lupinus perennis, Nelumbium speciosum, Orthosiphon stamineus benth, Panax ginseng, Paullinia cupana, Peumus boldus, Phyllacantha fibrosa, Piper methysticum, Piper nigrum, Prunella vulgaris, Prunus amygdalus dulcis, Rosmarinus officinalis, Rubus idaeus, Ruscus aculeatus* (extract of Butcher's broom)*, Salvia officinalis* L*, Sambucus nigra, Serenoa repens, Smilax aristolochiaefolia, Spirulina platensis* algae*, Taraxacum erythrospermum, Taraxacum officinale,* green tea*, Ulmus rubra, Uncaria tomentosa, Verbena officinalis, Vitex agnus-castus, Dysmorphococcus globosus,* among others, alverin, alverin citrate, dihydromyricetin, coenzyme A, lipase, cerulenin, rutin, glaucine, esculin, visnadine, caffeine, theophylline, theobromine, aminophylline, xanthine, carnitine, forskolin, escin, ruscogenin, hederin, triethanolamine iodide, AMPc synthesis inducing agents, Lanachrys® [INCI: *Chrysanthellum Indicum* Extract] marketed by Atrium/Unipex, Slim-Excess™ [INCI: Water, Butylene Glycol, Sodium Chloride, Hydrolyzed Carrageenan, Xanthan Gum], Sveltine™ [INCI: Water, Butylene Glycol, Carnitine, Lecithin, Caffeine, Carbomer, Salicylic Acid, Atelocollagen, *Centella Asiatica* Extract, Esculin, Sodium Chondroitin Sulfate], Peru Liana [INCI: *Uncaria Tomentosa* Extract] or Flavenger™ [INCI: Caprylic/Capric Triglyceride, Silica Dimethyl Silylate, Glyceryl Oleate, Quercetin Caprylate] marketed by BASF, Scopariane® [INCI: Sphacelaria Scoparia], Phyco R75™ [INCI: *Laminaria Digitata*], Pheoslim™ [INCI: *Phyllacantha Fibrosa* Extract], Buckwheat Wax [INCI: Polygonum fagopyrum] or Areaumat™ Samphira [INCI: *Crithmum Maritimum* Extract], Actiporine 8.G [Glycerine, Aqua, Jania rubens extract] marketed by Codif, Slimming Factor Karkade™ [INCI: *Hibiscus Sabdariffa*] marketed by Cosmetochem, Liposuctionine™ [proposed INCI: Acetyl Hexapeptide] marketed by Infinitec Activos, Xantalgosil [INCI: Acefylline Methylsilanol Mannuronate], Theophyllisilane CO [INCI: Methylsilanol Carboxymethyl Theophylline Alginate], Glutrapeptide® [INCI: Pyroglutamylamidoethyl Indole] or Cafeisilane C™ [INCI: Siloxanetriol Alginate, Caffeine, Butylene Glycol] marketed by Exsymol, [INCI: Polyglucuronic acid] marketed by Greentech, Visnadine [INCI: Visnadine] or Ginkgo Biloba Dimeric Flavonoids Phytosome [INCI: Phospholipids, *Ginkgo Biloba* Leaf Extract] marketed by Indena, Slimfit® LS 9509 [INCI: *Cecropia Obtusifolia* Bark Extract] marketed by Laboratoires Serobiologiques/Cognis/BASF, Silusyne™ [INCI: Soybean (*Glycine Soja*) Oil, Sorbitan Sesquioleate, Isohexadecane, Sodium Hyaluronate, Lauryldimonium Hydroxypropyl Hydrolized Soy Protein, Acetyl Hexapeptide-39] or Liporeductyl® [INCI: Water, Glycerin, Lecithin, Caffeine, Butcher broom (*Ruscus Aculeatus*) Root Extract, Maltodextrin, Silica, Tea-Hydroiodide, Propylene Glycol, Ivy (*Hedera Helix*) Extract, Carnitine, Escin, Tripeptide-1, Xanthan Gum, Carrageenan (Chondrus Crispus), Disodium EDTA] marketed by Lipotec/Lubrizol, Iso-Slim Complex™ [INCI: Soy Isoflavones, Caffeine, Carnitine, *Spirulina Platensis* Extract, Polysorbate 80, Alcohol, Phenoxyethanol, Aqua], Happybelle-PE™ [INCI: Lecithin, *Vitex Agnus* Castus Extract, Glycerin, Ascorbyl Tetraisopalmitate, Tocopherol, Caprylic/Capric Triglyceride, Cyclodextrin, Alcohol, Water] or AmaraShape™ [INCI: Lecithin, Caffeine, *Citrus Aurantium* Amara Extract, Pentylene Glycol, Alcohol, Water] marketed by Mibelle Biochemistry, Regu®-Slim [INCI: Maltodextrin, Caffeine, *Paullinia Cupana* Seed Extract, Carnitine, Microcrystalline Cellulose, Cysteic Acid, Pantetheine Sulfonate] or Regu®-Shape [INCI: Isomerized Linoleic Acid, Lecithin, Glycerin, Polysorbate 80] marketed by Pentapharm/DSM, Provislim™ [INCI: Propanediol, Water (Aqua), Fisetin, Raspberry Ketone], Myriceline [INCI: Dihydromyricetin], Drenalip™ [INCI: *Ruscus Aculeatus* Root Extract, *Citrus Medica* Limonum Peel Extract, Solidago Virgaurea Extract, Astragalus Membranaceus Root Extract] or Lipout™ [INCI: Plankton Extract] marketed by Provital, Actisculpt™ [INCI: *Commiphora Myrrha* Extract, *Coleus Forskohlii* Root Extract] marketed by Givaudan, Perfeline® [INCI: Water, Carnitine, Caffeine, *Ruscus Aculeatus* Extract] or CellActive® Shape [INCI: *Chlorella Vulgaris*/*Lupinus* Albus Protein Ferment, *Coleus Forskohlii*, Caffeine] marketed by Rahn, ProContour™ [INCI: Water, Alcohol, Lecithin, Caffeine, Carnitine, *Centella Asiatica* Leaf Extract, Potassium Phosphate, *Coleus Forskohlii* Root Extract] marketed by Rovi Cosmetics, Unislim™ [INCI: *Ilex Paraguariensis* (Leaf) Extract, Water, Butylene Glycol, *Coffea Arabica* (Coffee) Seed Extract (Bean), PEG-60 Almond Glycerides, Glycerin, Cetyl Hydroxyethylcellulose], Redulite™ [INCI: Glycerin, Aqua, Ethoxydiglycol, *Sambucus Nigra*, Sodium Polyacrylate], Pleurimincyl™ [INCI: Caffeine, *Bupleurum Chinensis* extract], Phytotal™ SL [INCI: Glycerin, *Verbena Officinalis* Extract, Butylene Glycol, *Sambucus Nigra* Flower Extract, *Eugenia Caryophyllus* (Clove) Flower Extract, Lecithin], Phytosonic™ [INCI: Aqua, Euglena Gracilis Extract, Caffeine, Glaucium Flavum Leaf Extract], Ovaliss™ [INCI: Glycerin, Aqua, Coco-glucoside, Caprylyl Glycol, Alcohol, Glaucine], Lipocare™ [INCI: Caffeine, Coenzyme A, *Bupleurum Chinensis* extract], Cyclolipase™ [INCI: Glyceryl Polymethacrylate, Water, Caffeine, Lipase, Adenosine Phosphate], Coaxel™ [INCI: Caffeine, Coenzyme A, Carnitine, Water, Glycerin], Bodyfit™ [INCI: Glycerin, Aqua (Water), Coco-Glucoside, Caprylyl Glycol, Alcohol, Glaucine], Intenslim™ [INCI: Globularia Cordifolia Callus Culture Extract, Zingiber Zerumbet Extract, Caffeine] or Vexel® [INCI: Aqua, Propylene glycol, Lecithin, Caffeine, Palmitoyl carnitine] marketed by Sederma/Croda, Voluform™ [INCI: Palmitoyl isoleucine], Adipoless™ [INCI: Butylene Glycol, *Chenopodium Quinoa* Seed Extract] marketed by Seppic, Slimactive® [INCI: *Peumus Boldus* Leaf Extract], Remoduline® [INCI: *Citrus Aurantium* Amara Flower Extract], Pro-Sveltyl [INCI: *Nelumbium Speciosum* Extract], Biosculptine® [INCI: Hydrolyzed *Celosia Cristata* Flower/Seed Extract, Hydrolyzed *Prunella Vulgaris* Extract], Affiness® [INCI: Hydrolyzed Coriandrum Sativum Fruit Extract, *Citrus Aurantium* Dulcis (Orange) Fruit Extract] or Stemsvelt [INCI: Water, Butylene Glycol, *Silybum marianum* extract] marketed by Silab, Delipidol™ [INCI: Tyrosyl Punicate], Guaraslim® [INCI: Butylene Glycol, Water, Caffeine, *Paullinia Cupana* Seed Extract, Ptychopetalum Olacoides Bark Extract] or Caobromine® [INCI: Theobroma Cocoa Shell Extract] marketed by Solabia, Abdoliance™ [INCI: Sucrose palmitate, Polysorbate 20, Glyceryl Linolenate, *Paullinia Cupana* Seed Extract, Maltodextrin, *Prunus Amygdalus* Dulcis (Sweet Almond) Oil, Lecithin, Water, *Citrus Aurantium* Amara (Bitter Orange) Peel Extract, Phenoxyethanol, Tocopherol], Betaphroline [INCI: *Tephrosia Purpurea* Seed Extract] or PRO-DG™ [INCI: Water, Plankton extract] marketed by Soliance, UCPeptide™ V [INCI: Water, Butylene Glycol, Pentapeptide] or ATPeptide™ IS [INCI: Tripeptide-3] marketed by Vincience/ISP among others, or mixtures thereof.

The composition can comprise at least one further extract with anti-oedema properties and improving vascular permeability/microcirculation, for example, chosen from Legactif™ [INCI: *Ruscus Aculeatus* Root Extract, *Citrus* Limon (Lemon) Peel Extract, Solidago Virgaurea (Goldenrod) Extract marketed by Provital, Legance™ [INCI: Zingiber Zerumbet Extract] and Eyeliss™ [INCI: Hesperidin Methyl Chalcone, Dipeptide-2, Palm itoyl Tetrapeptide-7] marketed by Sederma/Croda, Silidine® [I NCI: Porphyridium Cruentum Exudate] marketed by Greentech, Biophytex™ [INCI: Escin, *Ruscus Aculeatus* Root Extract, Ammonium Glycyrrhizate, *Centella Asiatica* Extract, Hydrolyzed Yeast Protein, *Calendula Officinalis* Flower Extract] marketed by L. Sérobiologiques/BASF, Cytobiol™ Lumin-Eye [INCI: Niacinamide, Fraxinus Excelsior Bark Extract, Silanetriol Potassium Citrate] marketed by Gattefossé, Regu®-Age [INCI: Hydrolyzed Rice Protein, Oxido Reductases, *Glycine Soja* (Soybean) Protein] marketed by DSM.

The composition can comprise at least one additional extract with depigmenting activity such as, for example and in a non-limiting sense, *Achillea millefolium*, *Aloe vera*, *Azadirachta indica*, *Osmunda japonica*, *Artocarpus incisus*, *Bidens pilosa*, *Broussonetia papyrifera*, *Chlorella vulgaris*, *Cimicifuga racemosa*, *Emblica officinalis*, *Glycyrrhiza glabra*, *Glycyrrhiza uralensis*, *Ilex purpurea*, *Ligusticum lucidum*, *Ligusticum wallichii*, *Mitracarpus scaber*, *Morinda citrifolia*, *Morus alba*, *Morus bombycis*, *Naringi crenulata*, *Prunus domesticus*, *Pseudostellariae radix*, *Rumex crispus*, *Rumex occidentalis*, *Sapindus mukurossi*, *Saxifraga sarmentosa*, *Scutellaria galericulata*, *Sedum sarmentosum Bunge*, *Stellaria medica*, *Triticum Vulgare*, *Uva ursi* or *Withania somnifera* extracts, among others, and/or at least one synthetic compound, extract or product derived from a biofermentation process with depigmenting activity such as, for example and in a non-limiting sense, Actiwhite™ LS9808 [INCI: Aqua, Glycerin, Sucrose Dilaurate, Polysorbate 20, *Pisum sativum* (Pea) extract], Dermawhite® NF LS9410 [INCI: Mannitol, Arginine HCl, Phenylalanine, Disodium EDTA, Sodium Citrate, Kojic Acid, Citric Acid, Yeast Extract] or Radianskin™ [INCI: Hydroxyphenoxy Propionic Acid] marketed by Laboratoires Serobiologiques/BASF, Lumiskin™ [INCI: Caprylic/Capric Triglyceride, Diacetyl-Boldine], Melaclear™ [INCI: Glycerin, Aqua, Dithiaoctanediol, Gluconic acid, Sutilains, Beta-carotene] or Etioline™ [INCI: Glycerin, Butylene Glycol, *Arctostaphylos uva ursi* Leaf Extract, *Mitracarpus scaber* Extract], O.D.A. White™ [INCI: Octadecenedioic Acid], Wonderlight™ [INCI: *Humulus Lupulus* (Hops) Strobile] marketed by Sederma, Sepiwhite™ MSH [INCI: Undecylenoyl Phenylalanine] or Seashine™ [INCI: Algae Extract, Undaria Pinnatifida Extract] marketed by Seppic, Achromaxyl™ [INCI: Aqua, *Brassica napus* extract] marketed by Vincience, Gigawhite™ [INCI: Aqua, Glycerin, *Malva sylvestris* (Mallow) Extract, *Mentha piperita* Leaf Extract, *Primula veris* Extract, *Alchemilla vulgaris* Extract, *Veronica officinalis* Extract, *Melissa officinalis* Leaf Extract, *Achillea millefolium* Extract], Melawhite® [INCI: Leukocyte Extract, AHA] (leukocyte extract, alpha hydroxy acids), Melfade®-J [INCI: Aqua, *Arctostaphylos uva-ursi* Leaf Extract, Glycerin, Magnesium Ascorbyl Phosphate] or Regu®-Fade [INCI: Resveratrol] marketed by Pentapharm/DSM, Albatin® [INCI: Amino ethyl phosphoric Acid, Butylene Glycol, Aqua] marketed by Exsymol, Tyrostat™-11 [INCI: Aqua, Glycerin, *Rumex occidentalis* Extract] or Melanostatine®-5 [INCI: Dextran, Nonapeptide-1] marketed by Atrium/Lucas Meyer, β-White [INCI: Oligopeptide-68] marketed by Unipex, Darkout™ [INCI: Hypoxis Rooperi Rhizome Extract, Caesalpinia Spinosa Gum] marketed by Provital, Vivillume™ [INCI: Strelitzia Nicolai Seed Aril Extract] marketed by Lonza, Superox-C™ [INCI: Terminalia Ferdinandiana Fruit Extract] marketed by Lucas Meyer, arbutin and its isomers, kojic acid and derivatives thereof, vitamin C and derivatives thereof such as, for example and in a non-limiting sense, 6-O-palmitoylascorbic acid, dipalmitoylascorbic acid, magnesium salt of ascorbic acid-2-phosphate (MAP), sodium salt of ascorbic-acid-2-phosphate (NAP), ascorbyl glucoside or ascorbyl tetraisopalmitate (VCIP) among others, retinol and derivatives thereof including tretinoin and isotretinoin, idebenone, hydroxybenzoic acid and derivatives thereof, flavonoids, soy extract, lemon extract, orange extract, ginkgo extract, cucumber extract, geranium extract, bearberry extract, carob bean extract, cinnamon extract, marjoram extract, rosemary extract, clove extract, soluble licorice extract, blackberry leaf extract, niacinamide, liquiritin, resorcinol and derivatives thereof, hydroquinone, α-tocopherol, γ-tocopherol, azelaic acid, resveratrol, mercury salts, linoleic acid, α-lipoic acid, dihydrolipoic acid, alpha hydroxy acids, beta hydroxy acids, ellagic acid, ferulic acid, cinnamic acid, oleanolic acid, aloesin and derivatives thereof and/or serine protease inhibitors such as, for example and in a non-limiting sense, tryptase, trypsin or PAR-2 inhibitors, among others.

The composition may comprise an additional agent for stimulating the synthesis of dermal or epidermal macromolecules selected, for example and not restricted to, from the group formed by collagen synthesis-stimulating agents, elastin synthesis-stimulation agents, decorin synthesis-stimulation agents, laminin synthesis-stimulation agents, chaperone synthesis-stimulating agents, sirtuin synthesis-stimulating agents, sirtuin activating agents, aquaporin synthesis-modulating agents, fibronectin synthesis-stimulating agent, agents that inhibit collagen degradation, agents that inhibit elastin degradation, agents that inhibit serine proteases such as kallikreins, leukocyte elastase or cathepsin G, agents stimulating fibroblast proliferation, agents stimulating adipocyte proliferation, agents that accelerate or delay adipocyte differentiation, and DNA repairing agents and/or DNA protecting agents, such as and not restricted to extracts of *Centella asiatica, Saccharomyces cerevisiae, Solanum tuberosum, Rosmarinus officinalis, Vaccinium angustifolium*, extract of the algae *Macrocystis pyrifera, Padina pavonica*, extract of soy, malt, flax, sage, red clover, kakkon, white lupin plants, hazelnut extract, maize extract, yeast extract, beech shoot extracts, leguminous seed extract, plant hormone extract such as gibberellins, auxins or cytokinins, among others, or extract of saline zooplankton, the fermentation product of milk with *Lactobacillus Bulgaricus*, asiaticosides and their derivatives, vitamin C and its derivatives, cinnamic acid and its derivatives, Matrixyl® [INCI: Palmitoyl Pentapeptide-3], Matrixyl® 3000 [INCI: Palmitoyl Tetrapeptide-3, Palmitoyl Oligopeptide] or Biopeptide CL™ [INCI: Glyceryl Polymethacrylate, Propylene Glycol, Palmitoyl Oligopeptide] marketed by Sederma/Croda, Antarcticine® [INCI: Pseudoalteromonas Ferment Extract], Decorinyl® [INCI: Tripeptide-10 Citrulline], Serilesine® [INCI: Hexapeptide-10], Lipeptide [INCI: Hydrolyzed Vegetable Protein], Aldenine® [INCI: Hydrolyzed Wheat Protein, Hydrolyzed Soy Protein, Tripeptide-1], Relistase™ [INCI: Acetylarginyltriptophyl Diphenylglycine], Thermostressine™ [INCI: Acetyl Tetrapeptide-22], Peptide AC29 [INCI: Acetyl Tripeptide-30 Citrulline], Diffuporine™ [INCI: Acetyl Hexapeptide-37], Silusyne™ [INCI: Soybean (*Glycine Soja*) Oil, Sorbitan Sesquioleate, Isohexadecane, Sodium Hyaluronate, Lauryldimonium Hydroxypropyl Hydrolyzed Soy Protein, Acetyl Hexapeptide-39] or Adifyline® [INCI: Acetyl Hexapeptide-38] marketed by Lipotec/Lubrizol, Drieline® PF [INCI: Yeast Betaglucan] marketed by Alban Muller, Phytovityl C® [INCI: Aqua, *Zea Mays* Extract] marketed by Solabia, Collalift® [INCI: Hydrolyzed Malt Extract] marketed by Coletica/Engelhard/BASF, Phytocohesine PSP™ [INCI: Sodium Beta-Sitosterol Sulfate] marketed by Vincience/ISP/Ashland, Neodermyl® [INCI: Methyl Glucoside Phosphate Proline Lysine Copper Complex], minerals such as calcium, among others, retinoids and their derivatives, isoflavonoids, carotenoids, in particular lycopene, pseudo-dipeptides, retinoids and their derivatives such as retinol or retinyl palmitate, among others, or heparinoids, among others.

In another aspect, the invention provides the use of the ferment extract as described herein in the preparation of a cosmetic composition for the cosmetic treatment and/or care of the skin, mucous membranes, hair and/or nails. The cosmetic treatment and/or care are as described herein.

In a fourth aspect of the invention, there is provided the use of the ferment extract of the invention for the cosmetic treatment and/or care of the skin, mucous membranes, hair and/or nails, wherein the ferment extract is present in a composition as described herein. Thus the fourth aspect of the invention relates to a cosmetic composition comprising a cosmetically effective quantity of the ferment extract from a strain of *Eupenicillium crustaceum* species for the cosmetic treatment and/or care of the skin, mucous membranes, hair and/or nails. The cosmetic composition can be as described herein. The cosmetic treatment and/or care are as described herein.

In a fifth aspect of the invention, there is provided a cosmetic method of treatment and/or care of the skin which comprises the administration of a cosmetically effective quantity of the ferment extract to the skin. The cosmetic treatment and/or care are as described herein. In one embodiment, the administration is topical. In one embodiment, the administration is transdermal. In one embodiment, topical or transdermal application is carried out by iontophoresis, sonophoresis, electroporation, mechanical pressure, osmotic pressure gradient, occlusive cure, microinjections, by needle-free injections by means of pressure, by microelectric patches, face masks or any combination thereof. In this aspect of the invention, the ferment extract may be present in a cosmetic composition, for example the cosmetic compositions described herein. Thus, the invention provides a cosmetic method of treatment and/or care of the skin which comprises the administration of a cosmetic composition comprising a cosmetically effective quantity of the ferment extract to the skin.

The frequency of the application or administration of the cosmetically effective quantity of the ferment extract can vary widely, depending on the needs of each subject, suggesting a range of application or administration from once per month to 10 times per day, from once per week to 4 times per day, from three times per week to three times per day, or once or twice per day.

In another aspect, this invention refers to a method of stimulation of collagen or elastin synthesis which comprises the administration of a cosmetically effective quantity of the ferment extract to human dermal fibroblast cells (skin).

Deposit of Biological Material

The strain of the species *Eupenicillium crustaceum* species was deposited at the Colección Española de Cultivos Tipo (CECT) (Edificio 3 CUE, Parc Científic Universitat de Valencia, Catedrático Agustin Escardino 9, 46980 Paterna, Valencia, Spain) under the conditions of the Budapest Treaty. The deposit was made on Mar. 20, 2014 and the deposit number was CECT-20901.

Each of the documents referred to above is incorporated herein by reference, including any prior applications, whether or not specifically listed above, from which priority is claimed. The mention of any document is not an admission that such document qualifies as prior art or constitutes the general knowledge of the skilled person in any jurisdiction. Except in the Examples, or where otherwise explicitly indicated, all numerical quantities in this description specifying amounts of materials, reaction conditions, molecular weights, number of carbon atoms, and the like, are to be understood as approximated, i.e., subject to a variability of ±5%, ±3%, ±1%, ±0.1%, or ±0.01% over the indicated value. It is to be understood that the upper and lower amount, range, and ratio limits set forth herein may be independently combined. Similarly, the ranges and amounts for each element of the technology described herein can be used together with ranges or amounts for any of the other elements.

The invention will now be illustrated by way of the following non-limiting examples.

EXAMPLES

Example 1

Preparation of the Ferment Extract Produced by the Strain of the *Eupenicillium crustaceum* with Deposit Number CECT-20901

A) Culture Process of the Strain of the *Eupenicillium crustaceum* with Deposit Number CECT-20901.

The strain of *Eupenicillium crustaceum* with deposit number CECT-20901 is cultivated in a fermenter, at 25° C. and at a pH of 7.5, in a culture medium containing water, 5 g/L of mannitol as source of carbon, 5 g/L of yeast extract, 5 g/L of soy peptone as sources of carbon and nitrogen, and 30 g/L of sea salts. The culture medium is inoculated with a 5% volume of a growing pre-culture. Fermentation is carried out for approximately 1 week, during which time the culture is fed with a sufficient air supply and stirred at stirring speeds of between 150 and 350 rpm.

B) Isolating the Ferment Extract Produced by the Strain of the *Eupenicillium crustaceum* with Deposit Number CECT-20901.

The *Eupenicillium crustaceum* cells are separated from the fermentation broth produced by step A), by continuous centrifugation at approximately 10,000 g. The supernatant broth is discarded and the *Eupenicillium crustaceum* cells are resuspended with ringer ¼ buffer (sodium chloride 2.25 g/L, potassium chloride 0.105 g/L, calcium chloride hexahydrate 0.12 g/L and sodium hydrogen carbonate 0.05 g/L). Following this, the cells are disrupted using a French press, with 2 cycles of operation at 40 KPsi. Next, the disrupted broth is extracted with isopropanol (with a volume ratio of isopropanol:disrupted broth of 4.7:1.0) in a stirred vessel over 3 h. Then, purification of the extract is performed by rotaevaporation of the extract at a temperature of 40-50° C. The dry weight of a sample the extract is then obtained by drying the (liquid) extract at 110° C. until a constant weight is achieved. Specifically, 2 mL of the extract was dried at 110° C. until constant weight is achieved. The constant weight of the dried extract was then used to calculate the dry weight concentration of the extract (dry weight of sample divided by weight of sample). This gives a value of 10% (W/W). In the examples, unless otherwise specified, the ferment extract is used in liquid (i.e. non-dried) form and, where the weight of the extract is referred to, this is the equivalent dry weight of the extract. The liquid extract is kept at a temperature of −20° C. until further use.

Example 2

Physicochemical Characterization of the Ferment Extract Produced by the Strain of the *Eupenicillium crustaceum* with Deposit Number CECT-20901

For the physicochemical characterization of the ferment extract, free amino acid and peptide analysis, carbohydrate analysis (phenol-sulfuric method), and lipid content analysis are performed for three different batches of the extract from the *Eupenicillium crustaceum* strain with deposit number CECT-20901. Batch 1 is obtained according to Example 1. Batches 2 and 3 are obtained according to the protocol described in Example 1, with the only difference being the use of discontinuous centrifugation equivalent to the continuous centrifugation conditions described in Example 1.

Free Amino Acid and Peptide Analysis

The same method is used for the analysis of free amino acids and peptides, with the difference that, for free amino acids, the hydrolysis (part i) is not performed, while for peptides it is performed.

i. Hydrolysis

The three batches of the ferment extract from the *Eupenicillium crustaceum* strain with deposit number CECT-20901 have the following dry weights: Batch 1 has a dry weight concentration of 10% (W/W); Batch 2 has a dry weight concentration of 18.4% (W/W); Batch 3 has a dry weight concentration of 19.9% (W/W).

For each batch, 25 mg of extract is placed in a 10 mL clean hydrolysis tube. 1 mL of 6N HCl+0.5% phenol are added and the mixture is heated to 110° C. for 24 hours. After that, the hydrolyzed sample is freeze-dried and resolved in 3 mL of 20 mM HCl.

ii. Amino Acids Derivatization.

The ACCQ-TAG Chemistry Package, based on AccQ●Fluor™ reagents (by WATERS Cromatografia, SA) is used to analyze amino acids. Preheat a heating block to 55° C. Tap Vial 2A lightly before opening to ensure all AccQ●Fluor™ Reagent Powder is at the bottom of the vial. Rinse a clean micropipette by drawing and discarding 1 mL of AccQ●Fluor™ Reagent Diluent from Vial 2B. Transfer 1 mL of AccQ●Fluor™ Reagent Diluent from Vial 2B to the AccQ●Fluor™ Reagent Powder in Vial 2A. Cap the vial 2A lightly and vortex for 10 seconds. The reconstituted AccQ●Fluor™ Reagent can be stored at room temperature in a desiccator for up to one week. After that, the calibration standards (containing between 2-100 pmol/μL of each amino acid, except cysteine which is at 1-50 pmol/μL) must be derivatized. Add 10 μL of calibration standard to the bottom of a clean sample tube and then add 70 μL of AccQ●Fluor™ Borate Buffer to the sample tube and vortex briefly. After that, add 20 μL of reconstituted AccQ●Fluor™ Reagent to the sample tube and vortex for several seconds. Incubate the mixture for 1 minute at room temperature and then heat the vial for 10 minutes at 55° C.

The same method is followed with the sample (substitute the calibration standard for the hydrolyzed sample). The column used for the analysis is an AccQ●Fluor™ Column (by WATERS) and the eluents are A) AccQ●Fluor™ Eluent A, and B) water/acetronitrile (40:60). The elution gradient starts at 0% of B and in 0.2 minutes increases to 2% of B. Then, at minute 15, the B concentration raises to 7% and, at minute 19, to 10% of B. The concentration of B continues increasing and, at minute 32, the concentration of B is 33%. Then, the concentration remains stable for 1 minute and after that the concentration of B increases to 100% in one minute. The 100% B is kept constant for three minutes in order to wash the column and finally the concentration back to 0% in order to start again. The flow is constant during all the analysis (1 mL/min) and the detection is done in a Fluorescence Detector ($\lambda_{ex}$=250 nm; $\lambda_{em}$=395 nm). The volume of injection is 10 μL and the oven temperature is 37° C.

The concentration of free amino acids (non-hydrolyzed sample) and peptides (total concentration from which the free amino acid concentration can be deducted) is calculated based on the calibration standards.

Carbohydrate Analysis (Phenol-Sulfuric Method)

Different standards of glucose are dissolved in water at different concentrations (between 20 and 500 μg/mL). Separately, 500 mg of phenol is dissolved in 10 mL of water in order to prepare a 5% phenol solution. Each batch of the ferment extract from the *Eupenicillium crustaceum* strain with deposit number CECT-20901, is prepared at 10 mg/mL in water. Then to 100 μL of this solution (or one of the standards), 100 μL of the 5% Phenol solution is added. The resultant solution is mixed and then 500 μL of sulfuric acid are added. After mixing, the reaction solution is incubated at 40° C. for 30 minutes. After that, the reaction is kept at room temperature for 15-20 minutes and the absorbance at 490 nm is read. With the basis of the calibration performed with the glucose standards, the carbohydrate concentration of the sample is calculated.

Lipid Content Analysis (Hexane Extraction Test)

5 g of each of Batches 1, 2 and 3 is dissolved in 10 mL of hexane. This solution is sonicated for 10 minutes and mixed in a vortex during 5 minutes. After that, the solution is centrifuged at 4000 rpm for 10 minutes in order to separate the solid. The liquid phase is recovered and then the solid is washed two times with 5 mL of hexane in order to extract all the lipids and then discarded. The organic phases are mixed and evaporated through nitrogen flow. After that, the solid obtained from the extraction is dried overnight in a freeze dryer and weighed. The concentration of lipids of the sample is calculated as the percentage of extracted weighed solid of the total sample weighed.

Lipid Content Analysis (Dichromate Test)

This method is an alternative to the hexane extraction test above and it is useful when there are small amounts of sample. 30 mg of each of Batches 1, 2 and 3 is dissolved in 2.5 mL of hexane. This solution is sonicated for 10 minutes and mixed in a vortex during 5 minutes. After that, the solution is centrifuged at 4000 rpm for 10 minutes in order to separate the solid. The liquid phase is recovered and then the solid is washed two times with 5 mL of hexane in order to extract all the lipids and then discarded. The organic phases are mixed and evaporated through nitrogen flow. After that, 3 mL of a reactive solution (2.5 g of $K_2Cr_2O_7$ are dissolved in 1 L of $H_2SO_4$ 36N) is added and heated to 100° C. for 45 minutes, mixing three times at different times. The sample is cooled to room temperature and an aliquot of 0.2 mL is diluted in 2.5 mL of water. After that, the absorbance at 350 nm is read and subtracted from a blank (the same treatment but without sample). The difference is proportional to the lipids amount. A standard sample is used in order to calculate the lipids in the samples in which the lipids content is unknown by comparing the absorbance difference.

The results from the free amino acid and peptide analysis, carbohydrate analysis, and lipid content analysis performed for the three different batches from the *Eupenicillium crustaceum* strain with deposit number CECT-20901 are presented in Table 1. The Lipid analysis results for Batch 1 were obtained using the hexane extraction test and those for Batches 2 and 3 were obtained using the dichromate test.

TABLE 1

Relative percentages by weight of free amino acids, peptides, carbohydrates, and lipids

|  | Batch 1 | Batch 2 | Batch 3 |
| --- | --- | --- | --- |
| peptides | 39.50% | 45.35% | 65.51% |
| free amino acids | 6.35% | 3.21% | 2.29% |
| carbohydrates | 21.36% | 21.99% | 13.34% |
| lipids | 32.79% | 29.45% | 18.86% |

HPLC Characterization

The ferment extract from the *Eupenicillium crustaceum* strain with deposit number CECT-20901 obtained according to Example 1 is diluted at 1 mg/mL with water/2-propanol (1:4, v/v) and is analyzed by HPLC with a size exclusion column TSKgel® G2000SWXL using the following conditions: the column is a TSKgel® G2000SWXL (7.8 mm ID×30.0 cm length, particle size 5 mm, pore size 125 Å). The eluent is 0.1M buffer phosphate pH 6.7+0.1M $Na_2SO_4$ and elution is kept isocratic using a flow of 1 mL/min. The detector is a UV ($\lambda$=220 nm), the injection is 25 μL and the oven temperature is 37° C.

The ferment extract shows peaks at 12 and 12.3 min, with a Gaussian distribution having a residence time between 10 and 20 minutes. 73.5% of the total area is located between 11 and 16 minutes, and 65% of the total area is located between 11 and 14 minutes. Using different standards with different molecular weights (thyroglobulin, 670,000 Da; albumin, 66,000 Da; ribonuclease, 13,700 Da and aminobenzoic acid, 122 Da) the molecular weight is calculated from the retention times. The peaks of the ferment extract (12 and 12.3 minutes) have a molecular weight between 325.9 Da and 229.2 Da, with a Gaussian distribution having an interval between 3,400 Da and 122 Da (this is the minimal weight of the standards) when calculated using the standards. 73.5% of the area under the Gaussian distribution has a molecular weight between 1053.9 and 122 Da when calculated with the standards.

Example 3

In Vitro Study of Type I Collagen Synthesis on Human Dermal Fibroblasts by Enzyme-Linked Immunosorbent Assay (ELISA)

Collagen type I is the principal type of collagen present in skin and is responsible for the strength and resiliency of skin. Collagen degenerates and lyses with age. Fibroblasts are the main cell producers of collagen. Thus, in vitro quantification of the induction of collagen synthesis as a result of treating human dermal fibroblasts (HDFa) with a candidate cosmetic active provides an indication as to whether or not that candidate will be effective as a skin anti-aging agent. If the candidate induces collagen synthesis this is an indicator that the candidate will be effective as a skin anti-aging agent.

Collagen induction by cosmetic products is evaluated by an Enzyme-Linked Immunosorbent Assay (ELISA).

Human Dermal Fibroblasts are treated with trypsin and $5 \times 10^4$ cells/well are seeded in 48-well plates. After 24 h (hours) incubation at 37° C. in 5% $CO_2$ humidified air, fresh medium is added with scalar dilutions of the extract of the strain of *Eupenicillium crustaceum* species with deposit number CECT20901, obtained in accordance with Example 1, at 20-0.1 μg/mL. Each concentration is tested in triplicate. Non-treated cells are seeded as controls in 48-well plates in 6 wells. The cells are incubated for an additional 48 h at 37° C. in 5% $CO_2$ humidified air. Then, well medium is collected so that it can be analyzed by ELISA. A standard curve is prepared with collagen type I from calf skin (Sigma) starting from a stock solution of 1 mg/ml. Standard curve dilutions and the supernatants collected from the cell culture treatments are transferred to 96-well plates. Collagen in the samples and in the standard curve dilutions coat the walls of the 96-well plates, which are kept at 4° C. in a humidified atmosphere overnight. Then, the well plates are washed three times with PBS-0.05% Tween-20 (v:v) (Sigma) and blocked for 1 h with 3% Bovine serum albumin (BSA) (w:v) (Sigma). After blocking, well plates are incubated with anti-collagen type I antibody (Sigma) for 2 h. After this incubation, the secondary antibody IgG-HRP (Molecular Probes) is added. At this time, the well plates are incubated with phosphatase substrate (OPD, Sigma) for 30 minutes under stirring. The reaction is stopped by adding 3M $H_2SO_4$ and absorbance at 490 nm is read in a microtiter plate reader TECAN GENios™. Collagen concentration is determined using a linear regression of type I collagen standard curve. Results of collagen synthesis increase versus non-treated cells (control) are shown in Table 2.

TABLE 2

The mean of the percentage of collagen type I with respect to the control for 3 assays

| Tested products | Concentration | Increase of type I Collagen synthesis vs control (%) |
|---|---|---|
| Extract obtained according to example 1 (Control) | 0 | 0% |
| Extract obtained according to example 1 | 20 µg/ml | 55.7% |
| Extract obtained according to example 1 | 10 µg/ml | 61.5% |
| Extract obtained according to example 1 | 5 µg/ml | 61.8% |
| Extract obtained according to example 1 | 2.5 µg/ml | 39.1% |
| Extract obtained according to example 1 | 1 µg/ml | 45.7% |
| Extract obtained according to example 1 | 0.5 µg/ml | 62.1% |
| Extract obtained according to example 1 | 0.2 µg/ml | 57% |
| Extract obtained according to example 1 | 0.1 µg/ml | 44.8% |

The results show that the extract of the invention promotes collagen Type I synthesis in human fibroblast cells.

Example 4

In Vitro Assay for Collagenase Activity

Collagen is the most abundant protein in skin connective tissue. It forms a mesh-like structure that helps to support new cells as they grow while providing needed flexibility. There is continual collagen synthesis and collagen degradation in the skin and the balance between these processes determines both the tensile strength and elasticity of the skin. Collagen degradation increase with age. Collagenase is a metalloproteinase that cleaves collagen into fragments. It follows that cosmetic actives that can inhibit collagenase activity may be effective in improving skin resistance and in acting as a skin anti-aging agent.

Collagenase activity is measured with EnzChek Gelatinase/Collagenase Assay Kit (Molecular Probes). The extract of the strain of *Eupenicillium crustaceum* species with deposit number CECT20901 is obtained in accordance with example 1 and is made into solutions of concentrations of 10 and 0 (control) mg/ml extract in reaction buffer. These solutions are added to a black 96-well microplate. Each concentration is tested in duplicate. Next, 20 µl of 1 mg/ml DQ Gelatin are added to each well and 100 µl of collagenase. The plate is incubated at room temperature, protected from light, for a 2-hour period and fluorescence is measured at multiple time points. The fluorescence is read at $\lambda_{exc}$=495 nm and $\lambda_{em}$=515 nm in a microtiter plate reader Tecan GENios™.

Table 3 shows the results which are displayed as the mean of the percentage of fluorescence with respect to control for a minimum of 2 assays.

TABLE 3

| Tested products | Concentration | Percentage of fluorescence respect to control (%) |
|---|---|---|
| Extract obtained according to example 1 (Control) | 0 | 100% |
| Extract obtained according to example 1 | 10 mg/ml | 81.7% |

The results show that the extract of the invention can inhibit collagenase activity.

Example 5

Evaluation of Elastin Induction on Human Dermal Fibroblasts

Elastin is a protein in connective tissue that is elastic and helps to keep skin flexible but tight, providing a bounce-back reaction if skin is pulled. Fibroblasts are the main cell producers of elastin. For this reason, in vitro quantification of elastin induction by cosmetic actives on human dermal fibroblasts provides information about potential anti-aging effects the cosmetic actives might have on the skin. If the cosmetic active induces collagen synthesis this is an indicator that the cosmetic active will be effective as a skin anti-aging agent.

Elastin induction by cosmetic actives is evaluated by the Fastin™ Elastin Assay (Tebu-Bio).

Human Dermal Fibroblasts are treated with trypsin and $3 \times 10^5$ cells/well are seeded in culture flasks. After incubation at 37° C. in 5% $CO_2$ humidified air for 72 hours, fresh medium is added with the extract of the strain of *Eupenicillium crustaceum* species with deposit number CECT20901, obtained in accordance with Example 1, at concentrations of 1, 0.1 and 0.01 µg/m L. Non-treated cells are seeded as negative controls for elastin synthesis. Each concentration is tested in duplicate. The cells are incubated for an additional 48 h at 37° C. in 5% $CO_2$ humidified air. Then, elastin is extracted from the cells. To do this, the cell medium is removed and cells are washed twice with PBS (Sigma) and then Cell Dissociation Solution (Sigma) is added. Cell suspension is transferred to microcentrifugate tubes and 1M Oxalic Acid is added and incubated for 1 h at 100° C. Once the elastin is solubilized, standards are prepared using α-elastin provided with the assay kit. From that point, samples and standards are processed together following kit instructions for elastin isolation and dye. Finally, the dye is extracted with the Dye Dissociation Reagent provided with the kit and the absorbance is measured at 540 nm in a microtiter plate reader TECAN GENios™.

In Table 4, the mean of the percentage of elastin induction with respect to the negative control is shown for a minimum of 3 assays.

TABLE 4

| Tested products | Concentration | Increase of elastin synthesis (%) |
|---|---|---|
| Extract obtained according to example 1 (Control) | 0 | 0% |
| Extract obtained according to example 1 | 1 µg/ml | 51.6% |
| Extract obtained according to example 1 | 0.1 µg/ml | 37.4% |
| Extract obtained according to example 1 | 0.01 µg/ml | 20.6% |

The results show that the extract of the invention promotes elastin synthesis in human dermal fibroblast cells.

Example 6

In Vitro Assay for Elastase Activity

Skin elasticity is a mechanical property influenced by elastin, a protein in the dermis which, together with collagen and glycosaminglycans, makes up the connective tissue. Metabolism of the proteins of the connective tissue decreases during the aging process and there is an ever greater presence of enzymes, principally elastases and collagenases, which are responsible for breaking down the elastin and the collagen. Thus one possible way to prevent the resultant loss of elasticity in the skin is to use active ingredients that are able to inhibit the activity elastase enzymes.

Elastase activity is measured with EnzChek Elastase Assay kit (Molecular Probes).

The extract of the strain of *Eupenicillium crustaceum* species with deposit number CECT20901, is obtained in accordance with Example 1, and is made into solutions of concentrations of 10, 5, 2, 1 and 0 (control) mg/ml extract in reaction buffer. The solutions are added to a black 96-well microplate. Each concentration is tested in duplicate. 50 µl of elastin working solution (1 mg/ml) is added to each well along with 100 µl of diluted enzyme. The microplate is incubated at room temperature, protected from light, for 4-hour period, and fluorescence is measured at multiple time points. The fluorescence is read at $\lambda_{exc}$=490 nm and $\lambda_{em}$=535 nm in a microtiter plate reader TECAN GENios™.

In Table 5 it is shown the mean of the percentage of fluorescence with respect to control for a minimum of 2 assays.

TABLE 5

| Tested products | Concentration | Percentage of fluorescence respect to control (%) |
|---|---|---|
| Extract obtained according to example 1 (Control) | 0 | 100 |
| Extract obtained according to example 1 | 10 mg/ml | 55.9 |
| Extract obtained according to example 1 | 5 mg/ml | 70.5 |
| Extract obtained according to example 1 | 2 mg/ml | 85.2 |
| Extract obtained according to example 1 | 1 mg/ml | 88.2 |

The results show that the extract of the invention can inhibit elastase activity.

Example 7

In Vitro Evaluation of the Formation of Advanced Glycation End Products

Glycation is the non-enzymatic reaction between a protein and a reducing sugar, such as glucose. The reaction forms what are known as advanced glycation end products (AGEs). Glycation alters the structure and function of the protein leading to dysfunction of the protein. In skin, glycation of collagen type I is believed to be linked to the development of skin dullness and the decrease in the skin elasticity. Glycation increases with age. Thus, cosmetic actives that are able to inhibit AGEs formation may have an effect on improving the elasticity and the luminosity of the skin. Such cosmetic actives would be effective skin anti-aging agents.

Glucose at 0.2M and collagen at 0.6% (v:v) are incubated in the presence of the extract of the strain of *Eupenicillium crustaceum* species with deposit number CECT20901, obtained in accordance with Example 1, at concentrations of collagen of 100, 1 and 0 (basal control) µg/ml. Each concentration is tested in duplicate. All solutions are incubated at 60° C., sampled at 0 and 3 days and the AGE formation is measured.

AGE formation between glucose and collagen type I is evaluated with the OxiSelect™ Advanced Glycation End Product Competitive ELISA Kit (Cell Biolabs). The samples or AGE-BSA standards are then added to the AGE conjugate preabsorbed ELISA plate. After a brief incubation, the anti-AGE polyclonal antibody is added, followed by an HRP (Horseradish Peroxidase) conjugated secondary antibody. After the incubation with the secondary antibody, well plates are incubated the Substrate Solution and the reaction is stopped by adding the Stop Solution. Absorbance is measured at 450 nm in a microtiter plate reader TECAN GENios™.

Table 6 shows the mean of the percentage of AGEs with respect to control for 3 assays.

TABLE 6

| Tested products | Concentration | Percentage of AGE with respect to the control (%) |
|---|---|---|
| Extract obtained according to example 1 (Control) | 0 | 100% |
| Extract obtained according to example 1 | 100 µg/ml | 70.3% |
| Extract obtained according to example 1 | 1 µg/ml | 80.6% |

The results show that at a concentration of 1 µg/ml, the extract of the invention inhibits the production of AGEs (the amount of AGEs produced is 80.6% of the amount produced when no extract is present). Increasing the amount of extract to 100 µg/ml results in increased inhibition of the production of AGEs, with the amount of AGEs produced falling to 70.3% of that produced when no extract is present.

Example 8

In Vitro Assay for Vascular Permeability

Although puffy eyes and bags under the eyes are caused by several contributing factors, excess fluid retention or oedema in the under eye area is believed to be one of the main causes. Fluid may build up for several reasons, including poor lymphatic circulation and increased capillary permeability. Therefore, cosmetic actives that decrease vascular permeability, thus reducing the amount of fluid that accumulates in interstitial compartment, could be good candidates for the cosmetic treatment of puffy eyes and bags under the eyes.

Human umbilical vein endothelial cells are treated with trypsin and $5 \times 10^4$ cells/well are seeded in inserts containing 1.0 μm symmetrical pores in 96-well tissue culture plates. After incubation at 37° C. in 5% $CO_2$ humidified air for 72 hours, the endothelial monolayer is formed and it occludes the membrane pores. At this point, fresh medium is added with the extract of the strain of *Eupenicillium crustaceum* species with deposit number CECT20901, obtained in accordance with Example 1, at concentrations of 5, 1 and 0.2 μg/mL. Non-treated cells are used as controls for vascular permeability. Each concentration is tested in triplicate. All cells are incubated for 24 hours at 37° C. and 5% $CO_2$.

After treatment, FITC-Dextran is added on top of the cells, allowing it to permeate through the cell monolayer. The extent of permeability is determined by measuring the fluorescence of the plate well solution at $\lambda_{exc}=485$ nm and $\lambda_{em}=535$ nm in a microtiter plate reader TECAN GENios™ after 20 minutes.

Table 7 shows the mean of the percentage of inhibition of vascular permeability with respect to control for a minimum of 3 assays.

TABLE 7

| Tested products | Concentration | Inhibition of vascular permeability (%) |
| --- | --- | --- |
| Extract obtained according to example 1 (Control) | 0 | 0% |
| Extract obtained according to example 1 | 5 μg/ml | 14% |
| Extract obtained according to example 1 | 1 μg/ml | 20.8% |
| Extract obtained according to example 1 | 0.2 μg/ml | 18.7% |

The results show that at the extract of the invention served to inhibit vascular permeability in that the amount of FITC-Dextran that permeated through the cell monolayer was up to 20.8% less when the extract is present compared to when no extract is present.

Example 9

In Vitro Assay for Influence in Bilirubin Degradation

Recently, bilirubin has been considered to be a factor in the presence of dark circles around the eye. It is well known that microcirculation around the eyes is one of the most important factors in dark circles formation. Blood vessel leakage in edemas around the eyes results in the accumulation of bilirubin and this produces dark circles with colors that can vary from yellow to blue. Thus a cosmetic active that can promote the degradation of bilirubin around the eyes could be a good cosmetic agent for helping reduce dark eye circles.

The test is performed in light-protected vials in order to avoid bilirubin oxidation. 1 mL of 0.1% bilirubin solution in water/2-propanol (1:1, v/v) is added to a 10 mL volumetric flask. After that, 4 mL of the extract of the strain of *Eupenicillium crustaceum* species with deposit number CECT20901, obtained in accordance with example 1, in a solution in water/2-propanol (1:1, v/v) at 25 mg/mL is added and then the flask is filled with water/2-propanol (1:1, v/v) to complete the 10 mL. In these conditions, the final concentration of the extract of the strain *Eupenicillium crustaceum* is 1%. At the same time, a negative control without the 25 mg/mL *Eupenicillium crustaceum* extract solution is prepared adding 1 mL of 0.1% Bilirubin solution and the volume of water/2-propanol (1:1, v/v) needed to complete the 10 mL of the volumetric flask. Once both solutions are prepared, they are transferred to light-protected glass vials and kept under constant agitation at room temperature. The concentration of bilirubin is followed by HPLC at different times.

The area of Conjugated Bilirubin at time zero is normalized to 100% in order to compare the three replicates. After 24 hours, the extract *Eupenicillium crustaceum* solution at 1% is able to reduce Bilirubin concentration in 19.36%. In Table 8 the normalized area of Bilirubin at different times is shown.

TABLE 8

| | NEGATIVE CONTROL | | 1% Extract obtained according to example 1 | |
| --- | --- | --- | --- | --- |
| Time (hours) | Normalized Area (%) | RSD (%) | Normalized Area (%) | RSD (%) |
| 0 | 100 | 0 | 100 | 0 |
| 2 | 93.86 | 9.62 | 96.35 | 8.56 |
| 4 | 89.68 | 3.31 | 89.27 | 10.92 |
| 20 | 90.82 | 5.60 | 72.53 | 8.15 |
| 24 | 93.22 | 2.25 | 75.17 | 4.02 |

The results show that after 24 hours, in the sample containing the extract of the invention, the amount of bilirubin present is 80.64% that of the control sample. Thus a reduction of bilirubin of 19.36% is achieved, with respect to normal degradation.

Example 10

Preparation of a Cosmetic Composition Comprising the Ferment Extract of the Strain of *Eupenicillium crustaceum* Species with Deposit Number CECT20901

A cosmetic composition is prepared, the ingredients of which are set out in table 9 below. In an appropriate container, the ingredients of Phase A are dissolved and Phase A1 ingredient is added little by little, with stirring until a total dispersion is achieved. Then the Phase A2 ingredient is added and the resultant mixture of ingredients was constantly stirred until they dissolved, and was heated to 70-75° C.

In another container, the phase B ingredients are melted at 70-75° C., and it was added to the mixture of ingredients of phases A, A1 and A2 little by little under turbine stirring.

Then, at 40° C., the ingredients of Phase C are added little by little, and stirring. Subsequently, the components of Phase D are added little by little, stirring until total dispersion, and the component of Phase E is added little by little with stirring until total dispersion. The pH was adjusted to 6.0-6.5 by addition of sodium hydroxide (q.s. sufficient quantity to adjust to this pH) under stirring (Phase F), obtaining a cosmetic composition with the proportions shown in table 9. The composition is a cream suitable for topical administration.

TABLE 9

| INGREDIENT (INCL name) | Weight | PHASE |
|---|---|---|
| WATER (AQUA) | 75.0000 | A |
| PENTYLENE GLYCOL | 5.0000 | A |
| BENZYL ALCOHOL | 1.0000 | A |
| CARBOMER | 0.5000 | A1 |
| POTASSIUM CETYL PHOSPHATE | 0.5000 | A2 |
| ETHYLHEXYL COCOATE | 2.5000 | B |
| GLYCERYL STEARATE | 2.0500 | B |
| CETEARYL ALCOHOL | 2.0500 | B |
| POTASSIUM PALMITOYL HYDROLYZED WHEAT PROTEIN | 0.9000 | B |
| C12-15 ALKYL BENZOATE | 5.0000 | B |
| DIMETHICONE | 1.0000 | B |
| PHENOXYETHANOL | 0.9000 | B |
| TOCOPHERYL ACETATE | 0.5000 | B |
| BUTYLENE GLYCOL | 1.879104 | C |
| WATER (AQUA) | 0.118683 | C |
| Ferment extract of the strain of *Eupenicillium crustaceum* species with deposit number CECT20901, obtained in accordance with Example 1 | 0.002213 | C |
| POLYACRYLAMIDE | 0.4000 | D |
| WATER (AQUA) | 0.3400 | D |
| C13-14 ISOPARAFFIN | 0.2000 | D |
| LAURETH-7 | 0.0600 | D |
| FRAGRANCE (PARFUM) | 0.1000 | E |
| SODIUM HYDROXIDE, WATER (AQUA) | 0.000 | F |
| | 100.000 | |

Example 11

In Vivo Study with the Composition of Example 10, Testing the Efficacy of the Ferment Extract of the Strain of *Eupenicillium crustaceum* Species with Deposit Number CECT20901 for the Treatment of Crow's Feet Wrinkles in Female Volunteers This study is carried out over 14 days with measurements being made initially at time=0 and then after 14 days. 20 volunteers are included and they are Caucasian females between 40 and 54 years old. Subjects apply the cream of Example 10 containing ferment extract of the strain of *Eupenicillium crustaceum* species with deposit number CECT20901 on one eye contour (left or right) and a placebo cream on the other eye contour. The creams are applied twice a day (morning and night). The subjects serve as their own reference and results obtained at different times are compared with those obtained at initial time zero. Moreover, results obtained with the active cream are compared with those obtained with placebo cream.

The efficacy of the product is assessed by the valuation of roughness parameters (Ra, Rz, Rt) of crow's feet (periorbital) wrinkles by means of a fringe projection system:

Ra (average roughness): arithmetic average of absolute height values

Rz (mean relief): distance between the highest and lowest point (5 peaks and 5 valleys)

Rt (total roughness): distance between the highest peak and the lowest valley (found along the evaluation length)

TABLE 10

Percentage variations with respect initial time of roughness parameters at 14 days.

| | VARIATIONS (%) | | |
|---|---|---|---|
| | Ra − (T14 − T0)/T0 | Rz − (T14 − T0)/T0 | Rt − (T14 − T0)/T0 |
| Active Cream | −9.0% | −8.7% | −9.8% |
| Placebo Cream | 7.7% | 6.2% | 6.4% |

The results shown in Table 10 demonstrate that, over a treatment period of 14 days of a cream containing ferment extract of the strain of *Eupenicillium crustaceum* species with deposit number CECT20901 is effective in reducing the roughness of skin due to periorbital wrinkles. That is, the size of the wrinkles is reduced and the wrinkled skin is made smoother. s (Ra, Rz, Rt) of crow's feet (periorbital) wrinkles by means of a fringe projection system: s (Ra, Rz, Rt) of crow's feet (periorbital) wrinkles by means of a fringe projection system:

Example 12

Preparation of a Cosmetic Composition Comprising the Ferment Extract of the Strain of *Eupenicillium crustaceum* Species with Deposit Number CECT20901

A cosmetic composition is prepared, the ingredients of which are set out in Table 11 below. In an appropriate container, the ingredients of phase A are dissolved and the phase A1 ingredient is added little by little, with stirring until a total dispersion is achieved. Then the phase A2 ingredient is added and this mixture of ingredients is constantly stirred until they dissolved, and was heated to 70-75° C.

In another container, the phase B ingredients are melted at 70-75° C., and the resultant mixture is added to the mixture of ingredients of phases A, A1 and A2, little by little, under turbine stirring.

Then, at 40° C., the ingredients of phase C are added little by little, and stirring.

Following this, the components of phase D are added little by little, stirring until total dispersion, and the component of phase E is added little by little and stirring until total dispersion. The pH was adjusted to 6.0-6.5 by addition of sodium hydroxide (q.s. sufficient quantity to adjust to this pH) under stirring (phase F), obtaining a cosmetic composition with the proportions shown in Table 11. The cosmetic composition is a cream suitable for topical use.

TABLE 11

| INGREDIENT (INCL name) | Weight | PHASE |
|---|---|---|
| WATER (AQUA) | 76.0000 | A |
| PENTYLENE GLYCOL | 5.0000 | A |
| BENZYL ALCOHOL | 1.0000 | A |
| CARBOMER | 0.5000 | A1 |
| POTASSIUM CETYL PHOSPHATE | 0.5000 | A2 |
| ETHYLHEXYL COCOATE | 2.5000 | B |
| GLYCERYL STEARATE | 2.0500 | B |
| CETEARYL ALCOHOL | 2.0500 | B |
| POTASSIUM PALMITOYL HYDROLYZED WHEAT PROTEIN | 0.9000 | B |
| C12-15 ALKYL BENZOATE | 5.0000 | B |
| DIMETHICONE | 1.0000 | B |
| PHENOXYETHANOL | 0.9000 | B |
| TOCOPHERYL ACETATE | 0.5000 | B |

TABLE 11-continued

| INGREDIENT (INCL name) | Weight | PHASE |
|---|---|---|
| BUTYLENE GLYCOL | 0.939552 | C |
| WATER (AQUA) | 0.0593415 | C |
| Ferment extract of the strain of *Eupenicillium crustaceum* species with deposit number CECT20901, obtained in accordance with example 1 | 0.0011066 | C |
| POLYACRYLAMIDE | 0.4000 | D |
| WATER (AQUA) | 0.3400 | D |
| C13-14 ISOPARAFFIN | 0.2000 | D |
| LAURETH-7 | 0.0600 | D |
| FRAGRANCE (PARFUM) | 0.1000 | E |
| SODIUM HYDROXIDE, WATER (AQUA) | 0.000 | F |
| | 100.000 | |

Example 13

In Vivo Study with the Composition of Example 12, Testing the Efficacy of the Ferment Extract of the Strain of *Eupenicillium crustaceum* Species with Deposit Number CECT20901 for the Treatment of Dark Circles Under the Eyes in Caucasian Skin Type Female Volunteers The study is carried out over 28 days with measurements made at initial time zero and then after 28 days. 21 volunteers are included and they are Caucasian females between 22 and 65 years old. The subjects apply the cream of the Example 12 containing ferment extract of the strain of *Eupenicillium crustaceum* species with deposit number CECT20901 on one eye contour (left or right) and a placebo cream on the other eye contour. The creams are applied twice a day (morning and night). The subjects serve as their own reference and results obtained at different times are compared with those obtained at initial time zero. Moreover, the results obtained with the active cream are compared with those obtained with placebo cream.

The efficacy of the product is assessed by digital photographs under cross polarized light of dark circles used for the analysis of the vascular component, results on Table 12.

TABLE 12

Percentage variations respect initial time of intensity of vascular component of the dark circle at 28 days

| | VARIATIONS (%)* (T + 28 days − T0)/T0 |
|---|---|
| Intensity - Active Cream | −11.5% |
| Intensity - Placebo Cream | −8.7% |

*calculated on the average values

The results shown in Table 12 demonstrate that, over a treatment period of 28 days of a cream containing ferment extract of the strain of *Eupenicillium crustaceum* species with deposit number CECT20901 is effective in reducing the darkness of (i.e. lightening in color) the skin in dark under-eye circles.

Example 14

Preparation of a Cosmetic Composition Comprising the Ferment Extract of the Strain of *Eupenicillium crustaceum* Species with Deposit Number CECT20901

A cosmetic composition is prepared, the ingredients of which are set out in table 13 below. In an appropriate container, the components of phase A are dissolved and the phase A1 component is added little by little, with stirring until a total dispersion is achieved. Then the phase A2 component is added and this mixture of ingredients is constantly stirred until they dissolved, and was heated to 70-75° C.

In another container, the phase B components are melted at 70-75° C., and the mixture is added to the mixture of the components of phases A, A1 and A2 little by little under turbine stirring.

Then, at 40° C., the ingredients of phase C are added little by little, with stirring. Subsequently, the components of phase D are added little by little, with stirring until total dispersion, and the component of phase E is added little by little and stirring until total dispersion. The pH was adjusted to 6.0-6.5 by addition of sodium hydroxide (q.s. sufficient quantity to adjust to this pH) under stirring (phase F), obtaining a cosmetic composition with the proportions shown in Table 13. The composition is a cream suitable for topical application.

TABLE 13

| INGREDIENT (INCL name) | Weight | PHASE |
|---|---|---|
| WATER (AQUA) | 71.4500 | A |
| PROPANEDIOL | 10.0000 | A |
| POTASSIUM SORBATE | 0.1000 | A |
| CARBOMER | 0.5000 | A1 |
| POTASSIUM CETYL PHOSPHATE | 0.5000 | A2 |
| ETHYLHEXYL COCOATE | 2.5000 | B |
| GLYCERYL STEARATE | 2.0500 | B |
| CETEARYL ALCOHOL | 2.0500 | B |
| POTASSIUM PALMITOYL HYDROLYZED WHEAT PROTEIN | 0.9000 | B |
| C12-15 ALKYL BENZOATE | 5.0000 | B |
| DIMETHICONE | 1.0000 | B |
| PHENOXYETHANOL | 0.3500 | B |
| TOCOPHERYL ACETATE | 0.5000 | B |
| BUTYLENE GLYCOL | 1.8582 | C |
| WATER (AQUA) | 0.1374 | C |
| Ferment extract of the strain of *Eupenicillium crustaceum* species with deposit number CECT20901, obtained in accordance with Example 1 | 0.0044 | C |
| POLYACRYLAMIDE | 0.4000 | D |
| WATER (AQUA) | 0.3400 | D |
| C13-14 ISOPARAFFIN | 0.2000 | D |
| LAURETH-7 | 0.0600 | D |
| FRAGRANCE (PARFUM) | 0.1000 | E |
| SODIUM HYDROXIDE, WATER (AQUA) | 0.000 | F |
| | 100.000 | |

Example 15

In Vivo Study with the Composition of Example 14, Testing Efficacy for the Treatment of Eye Bags in Female Volunteers The study is carried out over 28 days with measurements at initial time zero, then after 14 days and then after 28 days. 20 volunteers are included and they are Caucasian females between 41 and 66 years old. The subjects apply the cream of Example 14 containing ferment extract of the strain of *Eupenicillium crustaceum* species with deposit number CECT20901 on one eye contour (left or right) and placebo cream on the other eye contour. The cream is applied twice a day (morning and night). The subjects serve as their own reference and results obtained at different times are compared with those obtained at initial time. Moreover, results obtained with the active cream are compared with those obtained with placebo cream.

The efficacy of the product is assessed by evaluation of the volume of the eye bag by means of a fringe projection system; the results are presented in Table 14.

TABLE 14

Percentage variations with respect to initial time zero of eye bags volume at 14 and 28 days

| | VARIATIONS (%) | |
|---|---|---|
| | (T + 14 days − T0)/T0 | (T + 28 days − T0)/T0 |
| Volume - Active Cream | −5.7% | −8.2% |
| Volume - Placebo Cream | 1.1% | 1.5% |

The results shown in Table 14 demonstrate that, over treatment periods of 14 and 28 days of a cream containing ferment extract of the strain of *Eupenicillium crustaceum* species with deposit number CECT20901 is effective in reducing the volume of eye bags.

Example 16

In Vitro Assay for Melanogenesis on Human Epidermal Melanocytes

Melanogenesis is a process that occurs within melanocyte cells in skin and which results in the synthesis of melanin, the pigment determinant of skin color. In vitro melanin quantification induced by cosmetic actives provides information about their potential whitening effect.

Human melanocytes are treated with trypsin and are plated at a density of $2\times10^5$ cells/well on 6-well plates. After overnight incubation at 37° C., 5% $CO_2$, a first treatment with the extract of the strain of *Eupenicillium crustaceum* species with deposit number CECT20901, obtained in accordance with example 1, at 10, 5, 1 and 0.2 µg/mL is carried out. Non-treated cells are used as controls. Each concentration is tested in duplicate. The treatment is repeated on days 3, 6, 8 and 10. Finally cells are incubated at 37° C., 5% $CO_2$ for an additional 72 hours after the last treatment.

After the final incubation, cells are detached for cell counting and melanin measurement. Cell suspensions are centrifuged at 3000 rpm for 15 min and the pellet is dissolved in 1 ml of 1N NaOH with 10% DMSO (v:v). Cells are lysed for 2 h at 80° C. and centrifuged at 12000 rpm for 10 min. Melanin concentration is determined by measurement of absorbance at 450 nm in a plate reader TECAN GENios™ and values are normalized in respect to the number of cells per well. Melanin concentration is determined in picograms per cell (pg/cell) from a standard curve plotted with synthetic melanin at known concentrations.

In Table 15 the mean of the percentage of melanin with respect to control is shown for 3 assays.

TABLE 15

| Tested products | Concentration | Percentage of melanin (pg/cell) |
|---|---|---|
| Extract obtained according to example 1 (Control) | 0 | 100% |
| Extract obtained according to example 1 | 10 µg/ml | 38.7% |

TABLE 15-continued

| Tested products | Concentration | Percentage of melanin (pg/cell) |
|---|---|---|
| Extract obtained according to example 1 | 5 µg/ml | 45.7% |
| Extract obtained according to example 1 | 1 µg/ml | 53.7% |
| Extract obtained according to example 1 | 0.2 µg/ml | 55.3% |

The results shown in Table 15 demonstrate that the extract of the invention is effective in inhibiting melanogenesis (melanin synthesis) in human epidermal melanocytes.

Example 17

In Vitro Assay for Tyrosinase Activity

Melanogenesis is a process that occurs within melanocyte cells and results in the synthesis of melanin that is the pigment determinant of skin color. The key enzyme in melanogensis is tyrosinase. Tyrosinase initiates a cascade of reactions which convert tyrosine to melanin. Thus, cosmetic actives that are able to inhibit tyrosinase activity have potential as a skin whitening agent.

Tyrosinase activity is measured with the HumanLike Tyrosinase Assay Kit (Feldan). 200 µl/well of Reaction Mix is added to the microplate wells and samples of 10 µl of the extract of the strain of *Eupenicillium crustaceum* species with deposit number CECT20901, obtained in accordance with example 1, at 100, 10 and 1 µg/ml are added. Each concentration is tested in duplicate. Finally, 2 µl of enzyme are loaded. Wells without enzyme are used as blanks. The absorbance is read at λ=490 nm in a microtiter plate reader TECAN GENios™ (Genios, Tecan).

In Table 16 it is shown the mean of the percentage of absorbance with respect to the control for 3 assays.

TABLE 16

| Tested products | Concentration | Percentage of absorbance respect to control (%) |
|---|---|---|
| Extract obtained according to example 1 (Control) | 0 | 100% |
| Extract obtained according to example 1 | 100 µg/ml | 63.73% |
| Extract obtained according to example 1 | 10 µg/ml | 75.69% |
| Extract obtained according to example 1 | 1 µg/ml | 66.40% |

The results shown in Table 16 demonstrate that the extract of the invention is effective in inhibiting tyrosinase activity.

Example 18

Study of the Profile of the Gene Expression of Human Epidermal Melanocytes

Human melanocytes are treated with trypsin and are plated at a density of $2\times10^5$ cells/well on 6-well plates. After overnight incubation at 37° C., 5% $CO_2$, the first treatment with the extract of the strain of *Eupenicillium crustaceum* species with deposit number CECT20901, obtained in accordance with example 1, at 10 µg/mL is carried out. Non-treated cells are used as controls. Each concentration is tested in 10 wells. The treatment is repeated on days 3, 6, 8 and 10. Finally cells are incubated at 37° C., 5% $CO_2$ for an additional 72 hours after the last treatment.

After the last incubation, cells are lysed directly in the wells, and RNA is extracted and purified from each replica and each condition by means of the RNeasy™Plus Mini kit (Qiagen) following the manufacture's protocol. Briefly, the lysed cells are homogenized and the RNases are inactivated. The genomic DNA is removed from the samples by using gDNA Eliminator spin columns. Then, the samples are passed through special RNA binding columns and after several microcentrifugation washes to eliminate contaminants and impurities, the purified RNA is eluted with 50 μl of ultrapure water.

The purity, integrity and concentration of the RNA obtained are evaluated by means of spectrophotometry (Nanodrop) and with a bioanalyzer (Agilent Bioanalyzer). Four control samples and four treated samples are selected according to the results of purity and integrity.

Later, the labeling is carried out and the samples are hybridized in a human gene expression microarray (ASurePrint G3, Agilent).

The normalized values obtained with the treatment are compared with the normalized values obtained with the negative control to obtain genes with differential expression. Next, a parametric analysis of the data is carried out by means of the Bioconductor software. The values obtained are then evaluated by means of GSEA (Gene Set Analysis Enrichment) to group together the genes with differential expression in terms of Gene Ontology and Biological Routes.

The results of Log Fc obtained for selected genes involved in melanogenesis are shown in Table 17. Log FC is the logarithm (base 2) of fold change (FC). FC is used in analysis of gene expression data in microarray for measuring change in the expression level of a gene. The fold change is defined as a measure describing how much a quantity changes between the two experimental conditions under comparison, or as the ratio of intensities between the two experimental conditions under comparison. In this sense, the genes with negative values of Log FC are downregulated respect to the control whereas the genes with positive values for Log FC are upregulated respect to the control.

TABLE 17

LogFC values of the selected genes encoding enzymes involved in different reactions in the melanin synthesis Selected genes encoding enzymes involved in the melanin synthesis

| Symbol | Name | logFC |
| --- | --- | --- |
| TYR | tyrosinase | −0.42 |
| TYRP1 | tyrosinase-related protein 1 | −0.14 |
| DCT | dopachrome tautomerase | −0.98 |

TABLE 18

LogFC values of the selected genes encoding receptors, ligands and other proteins implicated in the regulatory control of the enzymes involved in the melanin synthesis Selected genes involved in the regulation of melanogenesis

| Symbol | Name | logFC |
| --- | --- | --- |
| ARRB2 | arrestin, beta 2 | −0.11 |
| PRKCA | protein kinase C, alpha | −0.56 |
| CAMK2G | calcium/calmodulin-dependent protein kinase II gamma | −0.21 |

TABLE 18-continued

LogFC values of the selected genes encoding receptors, ligands and other proteins implicated in the regulatory control of the enzymes involved in the melanin synthesis Selected genes involved in the regulation of melanogenesis

| Symbol | Name | logFC |
| --- | --- | --- |
| CREB3L2 | cAMP responsive element binding protein 3-like 2 | −0.21 |
| CREB3L4 | cAMP responsive element binding protein 3-like 4 | −0.40 |
| CREBBP | CREB binding protein | −0.22 |
| EP300 | E1A binding protein p300 | −0.20 |
| DKK1 | dickkopf 1 homolog (*Xenopus laevis*) | 3.26 |
| DVL2 | disheveled, dsh homolog 2 (*Drosophila*) | −0.47 |
| DVL3 | disheveled, dsh homolog 3 (*Drosophila*) | −0.25 |
| EDNRB | endothelin receptor type B | −1.11 |
| FZD10 | frizzled family receptor 10 | −0.62 |
| FZD8 | frizzled family receptor 8 | −0.60 |
| TCF7L1 | transcription factor 7-like 1 (T-cell specific, HMG-box) | −0.32 |

TABLE 19

LogFC values of the selected genes implicated in melanosomal organization or biogenesis Selected genes involved in melanosomal organization or biogenesis.

| Symbol | Name | logFC |
| --- | --- | --- |
| MLANA | melan-A | −0.69 |
| GPNMB | glycoprotein (transmembrane) nmb | −0.98 |
| PMEL | premelanosome protein | −0.56 |

The results shown in Table 18 demonstrate that the extract of the invention is able to upregulate or downregulate genes resulting in the inhibition of the melanogenesis. The results shown in Table 19 and Table 17 demonstrate that the extract of the invention is able to downregulate genes directly involved in melanosomal biogenesis and genes encoding the enzymes involved in the melanin synthesis. For all those effects in the gene regulation, the extract of the invention served to inhibit the melanogenesis process resulting in the whitening effect obtained.

Example 19

Preparation of a Cosmetic Composition of the Ferment Extract of the Strain of *Eupenicillium crustaceum* Species with Deposit Number CECT2090145

In an appropriate container, the ingredients of Phase A are dissolved and Phase A1 is added little by little, and stirring until a total dispersion is achieved. Then Phase A2 is added and this mixture of ingredients was constantly stirred until they dissolved, and is heated to 70-75° C.

In another container, the phase B ingredients are melted at 70-75° C., and it is added to the mixture of ingredients of phases A, A1 and A2 little by little under turbine stirring.

Then, at 40° C., the ingredients of Phase C are added little by little, and stirring.

Subsequently, the components of Phase D are added little by little, stirring until total dispersion, and the component of Phase E is added little by little and stirring until total dispersion. The pH is adjusted to 6.0-6.5 by addition of sodium hydroxide (q.s. sufficient quantity to adjust to this pH) under stirring (Phase F), obtaining a cosmetic composition with the proportions shown in Table 20.

TABLE 20

| INGREDIENT (INCI name) | weight | PHASE |
|---|---|---|
| WATER (AQUA) | 78.1000 | A |
| PENTYLENE GLYCOL | 3.0000 | A |
| BENZYL ALCOHOL | 0.4000 | A |
| CARBOMER | 0.5000 | A1 |
| POTASSIUM CETYL PHOSPHATE | 0.5000 | A2 |
| ETHYLHEXYL COCOATE | 2.5000 | B |
| GLYCERYL STEARATE | 2.0500 | B |
| CETEARYL ALCOHOL | 2.0500 | B |
| POTASSIUM PALMITOYL HYDROLYZED WHEAT PROTEIN | 0.9000 | B |
| C12-15 ALKYL BENZOATE | 5.0000 | B |
| DIMETHICONE | 1.0000 | B |
| PHENOXYETHANOL | 0.4000 | B |
| TOCOPHERYL ACETATE | 0.5000 | B |
| BUTYLENE GLYCOL | 1.8582 | C |
| WATER (AQUA) | 0.1374 | C |
| Extract of the strain of *Eupenicillium crustaceum* species with deposit number CECT20901, obtained in accordance with Example 1 | 0.0044 | C |
| WATER (AQUA) | 0.4700 | D |
| SODIUM ACRYLATES/BEHENETH-25 METHACRYLATE CROSSPOLYMER | 0.2750 | D |
| HYDROGENATED POLYDECENE | 0.2250 | D |
| LAURYL GLUCOSIDE | 0.0300 | D |
| FRAGRANCE (PARFUM) | 0.1000 | E |
| SODIUM HYDROXIDE, WATER (AQUA) | 0.000 | F |
| | 100.000 | |

Example 20

In Vivo Study with the Composition of Example 19, Testing the Efficacy of the Ferment Extract of the Strain of *Eupenicillium crustaceum* Species with Deposit Number CECT20901 for the Treatment of Age Spots and Skin Lightening Effect in Asiatic Skin Type Volunteers The study was carried out during 56 days with measurements at initial time and after 8 weeks of treatment. A panel of 22 female Asian volunteers between 38 and 53 years old applied the cream of the Example 19 on half face and placebo cream on the other half face, twice a day (morning and night). The subjects served as their own reference and results obtained at different times were compared with those obtained at initial time. Moreover, results obtained with the active cream were compared with those obtained with placebo cream.

The efficacy of the product was assessed by:

Measurements of skin color by spectral reflection of light, parameters L*, b* and ITA° (n=22), results are presented in Table 21

L*: Luminance parameter (from dark to light; skin lightness or luminosity)

b*: Chrominance parameter (from blue to yellow; skin yellowness)

ITA° (Individual Typology Angle): [Arc Tangent ((L*−50)/b*)]×180/3.14159

TABLE 21

Percentage variations versus initial time of Hyperpigmented and Non-hyperpigmented regions and contrast between both regions after 8 weeks of treatment

| | L* | | b* | | ITA° | |
|---|---|---|---|---|---|---|
| | Placebo cream | Active cream | Placebo cream | Active cream | Placebo cream | Active cream |
| Hyperpigmented | 1.57% | 2.48% | −0.26% | −3.28% | 8.20% | 15.30% |
| Non-hyperpigmented | 1.41% | 2.07% | −2.22% | −0.15% | 6.35% | 6.98% |
| Contrast | −1.00% | −3.95% | 24.32% | −34.58% | 1.79% | −12.68% |

Each parameter (L*, b* and ITA) is measured for each volunteer at different times (baseline and 8 weeks). Later the mean for each parameter is calculated and the % included in Table 21 is [(mean at 8 weeks 31 mean at 0 weeks)/ mean at 0 weeks] (%). Skin contrast is the value of a parameter on non-hyperpigmented region minus the value of a parameter on hyperpigmented region, i.e. contrast is a parameter related with homogeneity of skin color, if at end of treatment skin color is more homogeneous or not. Therefore, a negative value of contrast indicates an improvement of skin color homogeneity. The contrast is calculated for each volunteer and parameter as follows using L* as an example: L* contrast = L* non-hyperpigmented − L* hyperpigmented. The mean contrast value is calculated and used to calculate the evolution of contrast during treatment: % contrast = [(mean at 8 weeks − mean at 0 weeks)/ mean at 0 weeks]. This % is included in Table 21 under the heading contrast.

The results shown in Table 21 demonstrate that, over a treatment period of 8 weeks of a cream containing the ferment extract of the strain of *Eupenicillium crustaceum* species with deposit number CECT20901 is effective in increasing skin lightness (L*) and ITA° and reducing skin yellowness (b*) on hyper-pigmented region skin (age spots). Moreover, contrast between hyperpigmented and non-hyperpigmented region is decreased showing a whitening effect of the age spots.

Analysis of intensity of melanin on hyper-pigmented region by Reflectance Confocal Microscopy (n=2), results are shown in Table 22.

TABLE 22

Percentage variations versus initial time of the melanin intensity after 8 weeks of treatment.

| | Melanin intensity on hyperpigmented region |
|---|---|
| Placebo cream | −7.19% |
| Active cream | −61.12% |

The results shown in Table 22 demonstrate that, over a treatment period of 8 weeks of a cream containing the ferment extract of the strain of *Eupenicillium crustaceum* species with deposit number CECT20901 is effective in reducing the melanin intensity on hyper-pigmented region of the skin (age spots).

Example 21

Preparation of a Microemulsion Comprising the Ferment Extract of the Strain of *Eupenicillium crustaceum* Species with Deposit Number CECT20901

In an appropriate container, Docusate Sodium USP [INCI: DIETHYLHEXYL SODIUM SULFOSUCCINATE] and isostearic acid [INCI: ISOSTEARIC ACID] were mixed (phase A).

In another container, a mixture of the ferment extract of the strain of *Eupenicillium crustaceum* species with deposit number CECT20901, obtained in accordance with example 1, together with water [INCI: WATER (AQUA)] and BUTY- LENE GLYCOL 1,3 [INCI: BUTYLENE GLYCOL], was dissolved in ethanol [INCI: ALCOHOL] (phase B). Slowly, phase B was added to phase A under stirring. See Table 23

TABLE 23

| | INGREDIENT | % weight |
|---|---|---|
| A | DIETHYLHEXYL SODIUM SULFOSUCCINATE | 13.50 |
| A | ISOSTEARIC ACID | 76.50 |
| B | AQUA | 0.36 |
| B | BUTYLENE GLYCOL | 6.577 |
| B | Ferment extract of the strain of *Eupenicillium crustaceum* species with deposit number CECT20901, obtained in accordance with example 1 | 0.063 |
| B | ALCOHOL | 3.00 |

Example 22

Preparation of a Lipid Nanoparticle Composition Comprising the Microemulsion of Example 21

Water [INCI: WATER (AQUA)], Amigel® [INCI: *SCLE-ROTIUM* GUM], Zemea™ [INCI: PROPANEDIOL], Hyaluronic Acid [INCI: SODIUM HYALURONATE] and Phenoxyethanol [INCI: PHENOXYETHANOL] (phase A ingredients) were added in that order to an appropriate container and stirred until homogeneity was achieved.

The mixture comprising the microemulsion of example XX, refined soybean oil IP Ph. Eur. [INCI: *GLYCINE SOJA* (SOYBEAN) OIL], Arlacel 83 [INCI: SORBITAN SESQUIOLEATE], and Massocare HD [INCI: ISOHEXADECANE] (phase B ingredients) was added to another container.

Then, the mixture of the phase B ingredients was added to the mixture of the phase A ingredients under turbine stirring until an emulsion was formed.

The mixture was then homogenized with a Microfluidizer®, a high pressure homogenization system.

Finally, SENSOMER CT-400 [INCI: CASSIA HYDROXYPROPYLTRIMONIUM CHLORIDE] was slowly added under stirring (phase C). See table 24.

TABLE 24

| | INGREDIENT | % WEIGHT |
|---|---|---|
| A | WATER (AQUA) | q.s. 100 |
| A | SCLEROTIUM GUM | 0.50 |
| A | PROPANEDIOL | 5.00 |
| A | PHENOXYETHANOL | 2.6 |
| A | SODIUM HYALURONATE | 0.01 |
| B | Microemulsion of example 21 | 8.00 |
| B | *GLYCINE SOJA* (SOYBEAN) OIL | 12.00 |
| B | SORBITAN SESQUIOLEATE | 4.30 |
| B | ISOHEXADECANE | 5.50 |
| C | WATER (AQUA) | 2.00 |
| C | *CASSIA* HYDROXYPROPYLTRIMONIUM CHLORIDE | 0.50 |

Example 23

In Vitro Assay for Melanogenesis Inhibition on Reconstructed Human Pigmented Epidermis Hyperpigmentation is a disorder caused by exaggerated melanin production. Factors such as excessive solar exposure, aging, hormone changes, inflammation, allergies, among others, may cause an unbalance in the melanin production and distribution process, resulting in skin stains. Solar lentigines (SL) (also known as senile lentigo, sun-, liver-, or age spots) are circumscribed, pigmented macules, and are typically found on UV-exposed areas of the body. The molecular mechanism currently proposed for the appearance of solar lentigines involves the stimulation of epidermal signaling pathways including the Wnt pathway. WNT-1 is an activator of the Wnt signaling pathway involved in solar lentigines.

Reconstructed Human Pigmented Epidermis (RHPE), age day 10, phototype IV (SkinEthic laboratories) are removed from the agarose-nutrient solution in the multiwell plate immediately after arrival and placed in a 6-well plate in which each well had previously been filled with SkinEthic Growth Medium (SkinEthic laboratories). After overnight incubation at 37° C., 5% $CO_2$, a first treatment with recombinant human WNT-1 (Peprotech) at 200 ng/ml or with extract obtained according to Example 1 at 200 or 100 µg/ml with WNT-1 is carried out. The medium of each well is aspirated and fresh medium (containing either the recombinant human WNT-1 or the extract and the recombinant human WNT-1) is added. Each assay has control (basal conditions) wells in which the RHPE is treated with growth medium alone. The treatment is repeated every day until day 6, i.e. for five days, when the tissue models are embedded in Cryo-M-Bed (Bright).

After the 5 days of treatment, the tissue models are fixed in 4% paraformaldehyde (Sigma) for 3 hours at 4° C. and washed 4 times with Phosphate-buffered saline (PBS) (Sigma). Then, the samples are submitted to a sucrose gradient from 0.6 Molar to 2.3 Molar with incubations of 3 hours at room temperature. After the last incubation, the tissue models are embedded in Cryo-M-Bed. 10 µm sections are cut with a cryostat (Leica) and the melanin in the sections is stained using a Fontana-Masson Stain kit (Abcam).

The tissue sections are incubated with Ammoniacal Silver Solution pre-warmed at 58-60° C. for 0-60 minutes. Once the tissue sections become yellowish/brown in color, they are rinsed in several changes of distilled water. Then, the tissue sections are incubated in Gold Chloride Solution for 30 seconds and rinsed again. The tissue sections are incubated in Sodium Thiosulfate Solution for 1-2 minutes and rinsed for 2 minutes in running tap water, followed by two changes of distilled water. The sections are incubated in Nuclear Fast Red Solution for 5 minutes and rinsed for 2 minutes in running tap water, followed by two changes of distilled water. Finally, the sections are dehydrated in 3 changes of absolute alcohol, cleared and mounted in Neo-Mount® (Merck).

The sections are observed using a Zeiss optical microscope and the images are captured using Zen software. From each image, the amount of stained area is quantified.

Table 25 shows the fold-induction of melanin content, with respect to basal conditions, for a minimum of 3 assays.

TABLE 25

| Tested products | Extract Concentration | Fold-Induction (Mean ± SEM) |
|---|---|---|
| Basal conditions | 0 | 1 ± 0.03 |
| WNT-1(200 ng/ml) | 0 | 1.88 ± 0.27 |
| Extract obtained according to example 1 and WNT-1(200 ng/ml) | 200 µg/ml | 0.90 ± 0.12 |
| Extract obtained according to example 1 and WNT-1(200 ng/ml) | 100 µg/ml | 1.10 ± 0.10 |

The results show that the extract of the invention induces a significant decrease in melanin content in hyperpigmented human skin models at the tested concentrations.

Example 24

In Vitro Assay for Gene Expression Analysis

The aim of this study is to investigate the depigmentation efficacy of the extract obtained according to example 1 by evaluating the expression of genes of the melanogenesis pathway in darkly-pigmented melanocytes using a RT-qPCR array system.

Human Epidermal Melanocytes from a neonatal, darkly-pigmented donor (HEMn-DP) (Life Technologies) are trypsinized and are plated at a density of $3 \times 10^5$ cells/well on 6-well culture plates in Medium 254 supplemented with Human Melanocyte Growth Supplement-2 (HMGS-2-(PMA-free)) (Life Technologies). After overnight incubation at 37° C., 5% $CO_2$, a first treatment either with extract obtained according to Example 1 at 1 µg/ml or with medium alone (Basal conditions) is carried out. The medium of each well is aspirated and then fresh medium (containing either extract or medium alone) is added. The treatment is repeated on days 3, 6, 8 and 10. Finally, the cells are incubated at 37° C., 5% $CO_2$ for an additional 72 hours after the last treatment.

After the final incubation, the cells are lysed directly in the wells following the protocol described on the Aurum Total RNa Mini kit (BioRad) according to the manufacturer's protocol. The lysed cells are homogenized and the RNases are inactivated. Then, the samples are passed through special RNA binding columns and, after several microcentrifugation washes to eliminate contaminants and impurities, the purified RNA is eluted with 80 µl of elution solution. Quantification and analysis of the purity of the RNA samples is performed after RNA elution with a biophotometer (Eppendorf).

0.4 µg of high quality RNA are retrotranscribed with iScript™ Advanced (BioRad) in a final volume of 20 µl. Complete reaction mix is incubated in a thermal cycler (Eppendorf) at 42° C. for 30 minutes, the reaction is stopped at 85° C. for 5 minutes. Complementary DNA is amplified by qPCR in a real-time PCR thermocycler (BioRad) using SsoAdvanced Universal Inhibitor-Tolerant SYBR®green supermix (BioRad) in the human melanogenesis 96-well panel for use with SYBR® Green (BioRad). SYBR®Green binds to double-stranded DNA molecules and emits fluorescence which is quantified and is proportional to the amount of the product in the PCR reaction. Cycling conditions in BioRad CFX96 instrument are 95° C. for 3 minutes, followed by 40 cycles of denaturing at 95° C. for 5 seconds, annealing and elongation at 60° C. for 30 seconds. GAPDH (Glyceraldehyde 3-phosphate dehydrogenase), TBP (TATA box binding protein) and HRPT1 (hypoxanthine phosphoribosyltransferase 1) are used as endogenous controls. Fold change relative to the expression of the sample genes and reference genes is calculated using normalized expression ($\Delta\Delta(Ct)$) method with default threshold values using CFX Manager Software (BioRad).

Table 26 shows the relative levels of expression of the various genes indicated with respect to basal conditions for a minimum of 3 assays.

TABLE 26

| Symbol | Gene Name | Relative Levels (%) |
| --- | --- | --- |
| DCT | Dopachrome tautomerase | −7.35 |
| MLANA | Melan-A | −17.86 |
| TYR | Tyrosinase | −27.87 |
| TYRP1 | Tyrosinase-related protein 1 | −5.07 |
| DKK1 | Dickkopf homolog 1 | 385.02 |

The results show that the extract of the invention induces a significant decrease of the expression of melanogenesis genes in human melanocytes at the tested concentration, and a significant increase of DKK1 gene. The DKK1 gene codifies for a phagocytosis inhibitor that is also an inhibitor of the proliferation of melanocytes through the WNT pathway.

Example 25

In Vitro Assay for Tyrosinase Quantification by ELISA

The key enzyme in melanogenesis is tyrosinase, which initiates a cascade of reactions that convert tyrosine to the biopolymer melanin. This enzyme catalyzes two different reactions: the hydroxylation of mono-phenolic compounds to o-diphenols; and the oxidation of the o-diphenols to o-quinones. The enzyme converts tyrosine to 3,4-dhydroxyphenylalanine (L-dopa) and oxidizes L-dopa to form dopaquinone. L-dopa plays a prominent part in melanin biosynthesis.

Human Epidermal Melanocytes from a neonatal, darkly-pigmented donor (HEMn-DP) (Life Technologies) are trypsinized and are plated at a density of $5 \times 10^3$ cells/well on 96-well culture plates in Medium 254 supplemented with Human Melanocyte Growth Supplement-2 (HMGS-2-(PMA-free)) (Life Technologies). After overnight incubation at 37° C., 5% $CO_2$, a first treatment with extract obtained according to Example 1 at 50 or 10 µg/ml, or medium alone (basal conditions) is carried out. The medium of each well is aspirated and then fresh medium (containing either extract at 50 or 10 µg/ml, or medium alone) is added. The treatment is repeated on days 3, 6, 8 and 10. After 13 days of culture, an enzyme quantification is made using a Tyrosinase Cell-Based ELISA kit (Abnova) in the cultured cells. First, the cells are rinsed with Phosphate-buffered saline (PBS) twice and fixed with 4% formaldehyde for 20 minutes. Then, the cells are washed 3 times with Wash Buffer and Quenching Buffer is added and incubated for 20 minutes. The plates are washed again and blocked for 1 h with Blocking Buffer. After blocking, the well plates are incubated with Anti-tyrosinase Antibody or Anti-GAPDH Antibody for 16 hours. A total of 6 wells are used for each condition, three of them are incubated with the anti-tyrosinase antibody and the other three with the anti-GAPDH antibody. After this incubation, the secondary antibody (HRP-Conjugated Anti-Rabbit IgG for the wells incubated with Anti-tyrosinase Antibody or HRP-Conjugated Anti-Mouse IgG for the wells incubated with Anti-GAPDH Antibody) is added to corresponding wells and incubated for 1.5 hours. Then the well plates are incubated with TMB one-Step Solution for 30 minutes in the dark with gentle shaking. The reaction is stopped by adding the Stop Solution to each well. The absorbance at 450 nm is read in a microtiter plate reader (Clariostar®, BMG Labtech). The GAPDH signal is used for normalization of tyrosinase values.

Table 27 shows the mean percentage of tyrosinase level expression inhibition with respect to basal conditions for a minimum of 3 assays.

TABLE 27

| Tested products | Concentration | % of tyrosinase level inhibition (Mean ± SEM) |
|---|---|---|
| Basal conditions | 0 | 0 ± 2.4 |
| Extract obtained according to example 1 | 50 µg/ml | 48.93 ± 7.15 |
| Extract obtained according to example 1 | 10 µg/ml | 29.40 ± 7.70 |

The results show that the extract of the invention induces a significant reduction of tyrosinase protein levels in melanocyte cultures at the tested concentrations.

Example 26

In Vitro Assay for Microsphere-Based Phagocytosis

Skin pigmentation is determined by the transfer of melanin pigments from melanocytes to the neighboring keratinocytes and by their distribution pattern in suprabasal epidermal layers, as well as by the amount and type of melanin synthesized in the melanocytes. Melanin pigments are synthesized and stored in the specialized membrane-bound organelles termed melanosomes. Melanosomes are transported from the cell body to the periphery in melanocytes and are transferred from the dendrites of melanocytes into adjacent keratinocytes. After transfer, melanosomes are transported toward the nucleus to form a melanin cap that acts as an internal sunscreen in keratinocytes.

Supernatants of cultures of melanocytes are obtained from Human Epidermal Melanocytes from a neonatal, darkly-pigmented donor (HEMn-DP) (Life Technologies) seeded at a density of $3 \times 10^5$ cells/well in 6-well culture plates in Medium 254 (Life Technologies) supplemented with Human Melanocyte Growth Supplement-2 (HMGS-2-(PMA-free), Life Technologies). After 24 h, the medium is removed and the cells are incubated with extract obtained according to Example 1 at 1 µg/ml or with medium alone (supernatant control), for 13 days at 37° C. in a $CO_2$ incubator. The treatment is repeated on days 3, 6, 8 and 10. On day 13 the supernatants are collected and are used for treatment of Human Epidermal Keratinocytes.

Human Epidermal Keratinocytes (HEKa) (Life Technologies) are trypsinised and $3 \times 10^5$ cells/well are seeded on 12-well culture plates with coverslips pre-coated with Coating Matrix in Epilife medium supplemented with Epilife® Defined Growth Supplement (EDGS) (Life Technologies). After 24 hours incubation at 37° C. in 5% $CO_2$ humidified air, fresh medium containing 100 ng/ml DKK1 (R&D Systems) or the supernatant of the treated melanocytes is added. Each plate has control wells treated with medium alone (basal conditions). The plates are incubated for 30 minutes at 37° C., 5% $CO_2$. After the treatment, the medium is removed and the cells are incubated with FluoSpheres® carboxylate-modified red fluorescent microspheres (0.5 µm diameter, Life Technologies) at $3 \times 10^8$/ml for 4 hours. The microspheres are coated previously with Bovine serum albumin (BSA) (Sigma) according to manufacturer's instructions. After the incubation, the cells are washed with Phosphate-buffered saline (PBS) (Sigma) extensively to remove non-internalized microspheres, and fixed in 3.7% (V/V) paraformaldehyde (Sigma) for 10 minutes. Cells are washed with PBS and incubated in cold acetone for 3 minutes. Samples are blocked with 1% (W/V) BSA in PBS for 30 minutes. To visualize the cell outline, the cells are labeled with Alexa Fluor® 488 phalloidin (Life Technologies) for 20 minutes in the dark. The nuclei of cells are stained and coverslips mounted with ProLong® Gold antifade Reagent with DAPI (Life Technologies). The cells are observed using a Zeiss fluorescence microscope and images are captured using Zen software for quantification.

For quantitative analysis of the microsphere uptake, the number of microspheres and nuclei present in six microscopic fields randomly taken in three different experiments is counted for each condition. The number of microspheres of each image is normalized with the number of nuclei in each image.

Table 28 shows the mean fold-induction of phagocytosis with respect to basal conditions for a minimum of 3 assays.

TABLE 28

| Tested products | Concentration | Fold-Induction (Mean ± SEM) |
|---|---|---|
| Basal conditions | 0 | 1 ± 0.15 |
| Synthetic DKK1 | 100 ng/ml | 0.23 ± 0.06 |
| Supernatant control | 0 | 1 ± 0.13 |
| Extract obtained according to example 1 | 1 µg/ml | 0.31 ± 0.06 |

The results show that the extract of the invention induces significant inhibition of the microsphere uptake or phagocytosis of keratinocytes at the tested concentration.

The invention claimed is:

1. A cosmetic composition comprising a cosmetically effective quantity of a ferment extract from a strain of a *Eupenicillium crustaceum* species, and at least one cosmetically acceptable excipient, adjuvant and/or ingredient, wherein the ferment extract is produced by fermenting a strain of *Eupenicillium crustaceum* species in an aqueous culture medium and isolating the ferment extract from the aqueous culture medium or from cells of the *Eupenicillium crustaceum* species which have been separated out from the aqueous culture medium, wherein the ferment extract comprises relative species percentages of: 31 to 79 of peptides, 1 to 8% of free amino acids, 10 to 27% of carbohydrates, and 15 to 40% of lipids, with the condition that a sum of the percentages does not exceed 100%, and wherein the ferment extract is incorporated into a cosmetically acceptable delivery system or sustained release system selected from the group consisting of liposomes, mixed liposomes, oleosomes, niosomes, ethosomes, milliparticles, microparticles, nanoparticles and solid lipid nanoparticles, nanostructured lipid carriers, sponges, cyclodextrins, vesicles, micelles, mixed micelles of surfactants, surfactant-phospholipid mixed micelles, millispheres, microspheres and nanospheres, liposheres, millicapsules, microcapsules, nanocapsules, microemulsions and nanoemulsions or is adsorbed on a solid organic polymer or solid mineral support selected from the group consisting of talc, bentonite, silica, starch and maltodextrin.

2. A cosmetic composition comprising a cosmetically effective quantity of a ferment extract from a strain of a *Eupenicillium crustaceum* species, and at least one cosmetically acceptable excipient, adjuvant and/or ingredient, wherein the ferment extract is produced by fermenting a strain of *Eupenicillium crustaceum* species in an aqueous culture medium and isolating the ferment extract from the aqueous culture medium or from cells of the *Eupenicillium*

*crustaceum* species which have been separated out from the aqueous culture medium, wherein the extract comprises relative species percentages of: 31 to 79% of peptides, 1 to 8% of free amino acids, 10 to 27% of carbohydrates, and 15 to 40% of lipids, with the condition that a sum of the percentages does not exceed 100%, and wherein the composition is present in a formulation selected from the group consisting of multiple emulsions, liquid crystals, anhydrous compositions, oils, milks, balsams, foams, aqueous or oily lotions, aqueous or oily gels, creams, solutions, hydroalcoholic solutions, hydroglycolic solutions, hydrogels, liniments, sera, soaps, shampoos, conditioners, face masks, hairsprays, serums, polysaccharide films, ointments, mousses, pomades, pastes, powders, bars, pencils, sprays and aerosols.

3. A fabric, non-woven fabric, or medical device incorporating the cosmetic composition according to claim 1.

4. A composition according to claim 1, wherein said excipient, adjuvant and/or ingredient is selected from the group consisting of agents which diminish the sebum production, anti-seborrheic agents, mattifying agents, anti-acne agents, agents stimulating the synthesis of dermal or epidermal macromolecules and/or capable of inhibiting or preventing their degradation, collagen synthesis-stimulating agents, elastin synthesis-stimulation agents, decorin synthesis-stimulation agents, laminin synthesis-stimulation agents, defensin synthesis-stimulating agents, chaperone synthesis-stimulating agents, cAMP synthesis-stimulating agents, agents that modulate AQP-3, agents that modulate aquaporin synthesis, proteins from the aquaporin family, hyaluronic acid synthesis-stimulating agents, glycosaminoglycan synthesis-stimulating agents, fibronectin synthesis-stimulating agents, sirtuin synthesis-stimulating agents, heat shock proteins, heat shock protein synthesis-stimulating agents, agents which inhibit neuronal exocytosis, other anticholinergic agents, agents which inhibit muscular contraction, anti-aging agents, anti-wrinkle agents, antiperspirant agents, anti-inflammatory agents and/or analgesics, anti-itching agents, calming agents, anesthetic agents, inhibitors of acetylcholine-receptor aggregation, agents that inhibit acetylcholinesterase, skin relaxant agents, melanin synthesis stimulating or inhibiting agents, whitening or depigmenting agents, propigmenting agents, self-tanning agents, NO-synthase inhibiting agents, 5α-reductase inhibiting agents, lysyl- and/or prolyl hydroxylase inhibiting agents, antioxidants, free radical scavengers and/or agents against atmospheric pollution, reactive carbonyl species scavengers, antiglycation agents, antihistamine agents, antiviral agents, antiparasitic agents, emulsifiers, emollients, organic solvents, liquid propellants, skin conditioners, humectants, substances that retain moisture, alpha hydroxy acids, beta hydroxy acids, moisturizers, epidermal hydrolytic enzymes, vitamins, amino acids, proteins, pigments or colorants, dyes, biopolymers, gelling polymers, thickeners, surfactants, softening agents, emulsifiers, binding agents, preservatives, agents able to reduce or treat the bags under the eyes, exfoliating agents, keratolytic agents, desquamating agents, antimicrobial agents, antifungal agents, fungistatic agents, bactericidal agents, bacteriostatic agents, agents stimulating the synthesis of lipids and components of the stratum corneum, ceramides, fatty acids, agents that inhibit collagen degradation, agents that inhibit matrix metalloproteinases, agents that inhibit elastin degradation, agents that inhibit serine proteases, agents stimulating fibroblast proliferation, agents stimulating keratinocyte proliferation, agents stimulating adipocyte proliferation, agents stimulating melanocyte proliferation, agents stimulating keratinocyte differentiation, agents stimulating or delaying adipocyte differentiation, antihyperkeratosis agents, comedolytic agents, anti-psoriasis agents, DNA repair agents, DNA protecting agents, stem cell protecting agents, stabilizers, agents for the treatment and/or care of sensitive skin, firming agents, anti-stretch mark agents, binding agents, lipolytic agents or agents stimulating lipolysis, adipogenic agents, agents modulating PGC-1 α expression, agents modulating the activity of PPARγ, agents which increase or reduce the triglyceride content of adipocytes, anti-cellulite agents, agents which inhibit the activity of PAR-2, agents stimulating healing, coadjuvant healing agents, agents stimulating reepithelialization, coadjuvant reepithelialization agents, cytokine growth factors, agents acting on capillary circulation and/or microcirculation, agents stimulating angiogenesis, agents that inhibit vascular permeability, venotonic agents, agents acting on cell metabolism, agents which improve dermal-epidermal junction, agents inducing hair growth, hair growth inhibiting or retardant agents, hair loss retardant agents, preservatives, perfumes, odor absorbents and/or body odor masking deodorants, chelating agents, plant extracts, essential oils, marine extracts, agents obtained from a biotechnological process, mineral salts, cell extracts, sunscreens and organic or mineral photoprotective agents active against ultraviolet A and/or B rays and/or infrared A rays, and mixtures thereof.

5. A composition according to claim 1, wherein the effective quantity of the ferment extract in the composition, based on the extract dry weight, is 0.0000000001% to 20% by weight, based on the total weight of the composition.

6. The composition according to claim 1, wherein the effective quantity of the ferment extract in the composition, based on the extract dry weight, is at least 0.00005% by weight, based on the total weight of the composition.

7. The composition according to claim 1, wherein the ferment extract comprises free amino acids, peptides, carbohydrates and lipids.

8. The composition according to claim 1, wherein the ferment extract has a molecular weight of less than 3400 Da.

9. The composition according to claim 1, wherein the strain of *Eupenicillium crustaceum* species is a strain with deposit number CECT 20901.

10. The composition according to claim 1, wherein the excipient, adjuvant and/or ingredient is selected from the group consisting of
cosmetic carriers selected from the group consisting of peanut oil, soybean oil, mineral oil, sesame oil, castor oil, polysorbates, sorbitan esters, ether sulfates, sulfates, betaines, glycosides, maltosides, fatty alcohols, nonoxynols, poloxamers, polyoxyethylenes, polyethylene glycols, dextrose, glycerol, and digitonin;
humectants selected from the group consisting of glycerin, propylene glycol, butylene glycol, pentylene glycol, caprylyl glycol, lactic acid, urea, and sodium hyaluronate;
emollients and skin conditioning agents selected from dimethicone, glyceryl stearate, caprylic/capric triglyceride, cetearyl alcohol, lecithin, C12-15 alkyl benzoate, squalane, lanolin, behenyl alcohol, tocopheryl acetate, panthenol, Butyrospermum parkii butter, retinyl palmitate, and retinol;
surfactants selected from the group consisting of xanthan gum, sodium laureth sulfate, stearic acid, Polysorbate 20, Polysorbate 80, stearyl alcohol, cetyl alcohol, Steareth-2, Ceteareth-20, and cocamidopropyl betaine; and agents which increase the percutaneous absorption selected from the group consisting of dimethyl sulfoxide, dimethylacetamide, dimethylformamide, surfactants, azone (1-dodecylazacycloheptane-2-one), alcohol, urea, ethoxydiglycol, acetone, propylene glycol and polyethylene glycol.

11. A composition according to claim 2, wherein the effective quantity of the ferment extract in the composition, based on the extract dry weight, is 0.0000000001% to 20% by weight, based on the total weight of the composition.

12. The composition according to claim 2, wherein the ferment extract has a molecular weight of less than 3400 Da.

13. The composition according to claim 1, wherein the aqueous culture medium has a pH of about 7.5.

14. The composition according to claim 2, wherein the aqueous culture medium has a pH of about 7.5.

15. The composition according to claim 2, wherein the strain of *Eupenicillium crustaceum* species is a strain of *Eupenicillum crustaceum* species with deposit number CECT 20901.

16. A method of treatment or care of the skin, mucous membranes, hair or nails of an individual, comprising administering the composition according to claim 1 to the skin, mucous membranes, hair or nails of the individual.

17. The method according to claim 16, wherein the treatment and/or care includes at least one of:
depigmentation, whitening, or lightening in color of the skin, mucous membranes, hair and/or nails;
depigmentation, whitening, or the lightening in color of age spots; the depigmentation of or the whitening or lightening in color of the skin of dark eye circles;
maintenance or improvement of skin luminosity;
alleviation of the symptoms of skin aging;
treatment of skin wrinkles;
treatment of dark under-eye circles;
treatment of puffy eye;
treatment of eye bags;
smoothing out of or reduction of skin wrinkles;
reduction in volume of a puffy eye or of eye bags;
maintenance or improvement of skin elasticity; and
maintenance or improvement of skin resistance, firmness or tensile strength.

18. The method according to claim 16, wherein the treatment and/or care promotes collagen production, promotes elastin production, inhibits collagenase activity, inhibits elastase activity, inhibits the production of AGEs, inhibits vascular permeability, inhibits melanin formation, inhibits tyrosinase activity and/or promotes the breakdown of bilirubin in the skin.

19. The method according to claim 16, wherein the administration comprises topical administration of the composition to the individual.

20. A method of treatment or care of the skin, mucous membranes, hair or nails of an individual, comprising administering the composition according to claim 2 to the skin, mucous membranes, hair or nails of the individual.

* * * * *